(12) United States Patent
Zlokovic

(10) Patent No.: US 7,695,903 B2
(45) Date of Patent: Apr. 13, 2010

(54) LOW-DENSITY LIPOPROTEIN RECEPTOR RELATED PROTEIN-1 (LRP-1)IN CLEARANCE OF ALZHEIMER'S AMYLOID-BETA PEPTIDE FROM THE CENTRAL NERVOUS SYSTEM

(75) Inventor: Berislav V. Zlokovic, Rochester, NY (US)

(73) Assignee: The University of Southern California, Los Angeles, CA (US)

( * ) Notice: Subject to any disclaimer, the term of this patent is extended or adjusted under 35 U.S.C. 154(b) by 1641 days.

(21) Appl. No.: 10/296,168

(22) PCT Filed: May 23, 2001

(86) PCT No.: PCT/US01/16561

§ 371 (c)(1),
(2), (4) Date: Jun. 30, 2003

(87) PCT Pub. No.: WO01/90758

PCT Pub. Date: Nov. 29, 2001

(65) Prior Publication Data

US 2005/0239062 A1    Oct. 27, 2005

Related U.S. Application Data

(60) Provisional application No. 60/206,428, filed on May 23, 2000, provisional application No. 60/246,268, filed on Nov. 6, 2000.

(51) Int. Cl.
*C12Q 1/68* (2006.01)
*G01N 33/567* (2006.01)
*A61K 49/00* (2006.01)

(52) U.S. Cl. .............................. 435/6; 435/7.21; 424/9.1

(58) Field of Classification Search ........................ None
See application file for complete search history.

(56) References Cited

U.S. PATENT DOCUMENTS

| | | | |
|---|---|---|---|
| 4,758,583 | A | 7/1988 | Cerami et al. |
| 4,900,747 | A | 2/1990 | Vlassara et al. |
| 5,202,424 | A | 4/1993 | Vlassara et al. |
| 5,316,754 | A | 5/1994 | Vlassara et al. |
| 5,766,856 | A | 6/1998 | Imani et al. |
| 5,864,018 | A | 1/1999 | Morser et al. |
| 5,962,245 | A | 10/1999 | Li et al. |
| 6,156,311 | A | 12/2000 | Strickland et al. |
| 6,410,598 | B1 | 6/2002 | Vitek et al. |
| 6,413,512 | B1 | 7/2002 | Houston et al. |
| 6,447,775 | B1 | 9/2002 | Strickland et al. |
| 6,472,140 | B1 | 10/2002 | Tanzi et al. |
| 2004/0115671 | A1* | 6/2004 | Zlokovic et al. ............... 435/6 |
| 2004/0259159 | A1* | 12/2004 | Zlokovic ................... 435/7.1 |
| 2005/0170359 | A1* | 8/2005 | Zlokovic ..................... 435/6 |

FOREIGN PATENT DOCUMENTS

| | | |
|---|---|---|
| WO | 97/04794 A | 2/1997 |
| WO | WO 02/14519 | 2/2002 |

OTHER PUBLICATIONS

Uden et al. Mol. Cell. Neurosci. 1999. 14, 129-140.*
Urmoneit et al. Lab Invest. 1997. 77: 157-66.*
Mackie et al. J. Neurochem. 1998. 70: 210-215.*
Tanzi et al. Neuron 2004. 43: 605-608.*
Blacker et al. Nat. Genet. Aug. 1998; 19:357-60.*
Deane et al. "RAGE (Yin) versus LRP (Yang) balance regulates Alzheimer amyloid β-peptide clearance through transport across the blood-brain barrier" Stroke 35:2628-2631 (2004).
DeMattos et al. "Brain to plasma amyloid-β efflux: A measure of brain amyloid burden in a mouse model of Alzheimer's disease" Science 295:2264-2267 (2002).
Hardy et al. "The amyloid hypothesis of Alzheimer's disease: Progress and problems on the road to therapeutics" Science 297:353-356 (2002).
Herz et al. "LRP: A multifunctional scavenger and signaling receptor" J. Clin. Invest. 108:779-784 (2001).
Hsiao et al. "Correlative memory deficits, $A^\beta$ elevation, and amyloid plaques in transgenic mice" Science 274:99-103 (1996).
Hyman et al. "Role of the low-density lipoprotein receptor-related protein in beta-amyloid metabolism and Alzheimer disease" Arch. Neurol. 57:646-650 (2000) (abstract).
Kang et al. "Genetic association of the low-density lipoprotein receptor-related protein gene (LRP), and apolipoprotein E receptor, with late-onset Alzheimer's disease" Neurology 49:56-61 (1997).
Kang et al. "Modulation of amyloid β-protein clearance and Alzheimer's disease susceptibility by the LDL receptor-related protein pathway" J. Clin. Invest. 106:1159-1166 (2000).
Kounnas et al. "LDL receptor-related protein, a multifunctional ApoE receptor, binds secreted β-amyloid precursor protein and mediates its degradation" Cell 82:331-340 (1995).

(Continued)

*Primary Examiner*—Christine J Saoud
*Assistant Examiner*—Chang-Yu Wang
(74) *Attorney, Agent, or Firm*—Nixon & Vanderhye P.C.

(57) ABSTRACT

Brain endothelial low-density lipoprotein receptor related protein-1 (LRP-1) mediates vascular clearance of Alzheimer's amyloid-β peptide (Aβ) from the brain. Transport of Aβ occurs across the blood-brain barrier (BBB) to the systemic circulation, but the brain endothelium is compromised in Alzheimer's disease. The invention is used to diagnose the disease in symptomatic and asymptomatic individuals, to identify those at risk for disease or already affected thereby, to determine the stage of disease or its progression, to intervene earlier in or alter the disease's natural history, to provide a target for therapeutic or prophylactic treatments, to screen drugs or compare medical regimens, to determine the effectiveness of a drug or medical regimen, or any combination thereof.

11 Claims, 9 Drawing Sheets

OTHER PUBLICATIONS

Lorenzo et al. "Amyloid beta interacts with the amyloid precursor protein: A potential toxic mechanism in Alzheimer's disease" Nat. Neurosci. 3:460-464 (2000) (abstract).

Melman et al. "Proteasome regulates the delivery of LDL receptor-related protein into the degradation pathway" Mol. Biol. Cell 13:3325-3335 (2002).

Pietrzik et al. "The cytoplasmic domain of the LDL receptor-related protein regulates multiple steps in APP processing" EMBO J. 21:5691-5700 (2002).

Takahashi et al. "Intraneuronal Alzheimer Aβ42 accumulates in multivesicular bodies and is associated with synaptic pathology" Am. J. Pathol. 161:1869-1879 (2002).

Ulery et al. "Modulation of β-amyloid precursor protein processing by the low density lipoprotein receptor-related protein (LRP)" J. Biol. Chem. 275:7410-7415 (2000).

Ulery et al. "LRP in Alzheimer's disease: Friend or foe?" J. Clin. Invest. 106:1077-1079 (2000).

Uden et al. "LDL receptor-related protein (LRP) in Alzheimer's disease: Towards a unified theory of pathogenesis" Microsc. Res. Tech. 15:268-272 (2000) (abstract).

Van Uden et al. "Increased extracellular amyloid deposition and neurodegeneration in human amyloid precursor protein transgenic mice deficient in receptor-associated protein" J. Neurosci. 22:9298-9304 (2002).

Vinters et al. "Amyloidosis of cerebral arteries" Adv. Neurol. 92:105-112 (2003).

Willnow et al. "Functional expression of low density lipoprotein receptor-related protein is controlled by receptor-associated protein in vivo" Proc. Natl. Acad. Sci. USA 92:4537-4541 (1995).

Willnow et al. "RAP, a specialized chaperone, prevents ligand-induced ER retention and degradation of LDL receptor-related endocytic receptors" EMBO J. 15:2632-2639 (1996).

Wolozin et al. "A fluid connection: Cholesterol and Aβ" Proc. Natl. Acad. Sci. USA 98:5371-5373 (2001).

Zerbinatti et al. "Increased soluble amyloid-β peptide and memory deficits in amyloid model mice overexpressing the low-density lipoprotein receptor-related protein" Proc. Natl. Acad. Sci. USA 101:1075-1080 (2004).

Deane et al. "RAGE mediates amyloid-β peptide transport across the blood-brain barrier and accumulation in brain" Nature Medicine 9:907-913 (2003).

DeMattos et al. "Peripheral anti-Aβ antibody alters CNS and plasma Aβ clearance and decreases brain Aβ burden in a mouse model of Alzheimer's disease" Proc. Natl. Acad. Sci. USA 98:8850-8855 (2001).

Ghersi-Egea et al. "Fate of cerebrospinal fluid-borne amyloid β-peptide: Rapid clearance into blood and appreciable accumulation by cerebral arteries" J. Neurochem. 67:880-883 (1996).

Ghilardi et al. "Intra-arterial infusion of [$^{125}$I]Aβ1-40 labels amyloid deposits in the aged primate brain in vivo" NeuroReport 7:2607-2611 (1996).

Iwata et al. "Identification of the major Aβ$_{1-42}$-degrading catabolic pathway in brain parenchyma: Suppression leads to biochemical pathological deposition" Nature Medicine 6:143-150 (2000).

Lucarelli et al. "Expression of receptors for native and chemically modified low-density lipoproteins in brain microvessels" FEBS Letters 401:53-58 (1997).

Mackic et al. "Human blood-brain barrier receptors for Alzheimer's amyloid-β 1-40. Asymmetrical binding, endocytosis, and transcytosis at the apical side of brain microvascular endothelial cell monolayer" J. Clin. Invest. 102:734-743 (1998).

Mackic et al. "Cerebrovascular accumulation and increased blood-brain barrier permeability to circulating Alzheimer's amyloid β peptide in aged squirrel monkey with cerebral amyloid aniopathy" J. Neurochem. 70:210-215 (1998).

Maness et al. "Passage of human amyloid β-protein 1-40 across the murine blood-brain barrier" Life Sciences 55:1643-1650 (1994).

Martel et al. "Isoform-specific effects of apolipoprioteins E2, E3, and E4 on cerebral capillary sequestration and blood-brain barrier transport of circulating Alzheimer's amyloid β" J. Neurochem. 69:1995-2004 (1997).

Mattson et al. "Amyloid ox-tox transducers" Nature 382:674-675 (1996).

Poduslo et al. "Permeability and residual plasma volume of human, Dutch variant, and rat amyloid β-protein 1-40 at the blood-brain barrier" Neurobiol. Dis. 4:27-34 (1997).

Schmidt et al. "Receptor for advanced glycation end products (AGEs) has a central role in vessel wall interactions and gene activation in response to circulating AGE proteins" Proc. Natl. Acad. Sci. USA 91:8807-8811 (1994).

Yan et al. "RAGE and amyloid-β peptide neurotoxicity in Alzheimer's disease" Nature 382:685-691 (1996).

Yan et al. "Receptor-dependent cells stress and amyloid accumulation in systemic amyloidosis" Nature Medicine 6:643-651 (2000).

Zlokovic "Can blood-brain barrier play a role in the development of cerebral amyloidosis and Alzheimer's disease pathology" Neurobiol. Dis. 4:23-26 (1997).

Zlokovic et al. "Glycoprotein 330/megalin: Probable role in receptor-mediated transport of apolipoprotein J alone and in a complex with Alzheimer disease amyloid β at the blood-brain and blood-cerebrospinal fluid barriers" Proc. Natl. Acad. Sci. USA 93:4229-4234 (1996).

Zlokovic et al. "Clearance of amyloid β-peptide from brain: Transport or metabolism?" Nature Medicine 6:718-719 (2000).

Int'l Search Report dated Jun. 24, 2002 for Appln. No. PCT/US01/16561.

Qiu et al; "ALPHA2-Macroglobulin Enhances the Clearance of Endogenous Soluble Beta-Amyloid Peptide Via Low-Density Lipoprotein Receptor-Related Protein in Cortical Neurons"; Journal of Neurochemistry, vol. 73, No. 4, Oct. 1999, pp. 1393-1398, XP008003745.

Jordan et al; "Isoform-Specific Effect of Apolipoprotein E on Cell Survival and Beta-Amyloid-Induced Toxicity in Rat Hippocampal Pyramidal Neuronal Cultures"; Journal of Neuroscience, New York, NY, US, vol. 18, No. 1, Jan. 1, 1998, pp. 195-204, XP002930147.

Narita et al; "ALPHA2-Macroglobulin Complexes With and Mediates the Endocytosis of Beta-Amyloid Peptide Via Cell Surface Low-Density Lipoprotein Receptor-Related Protein"; Journal of Neurochemistry, New York, NY, vol. 69, No. 5, 1997, pp. 1904-1911, XP000921049.

Shibata et al; "Clearance of Alzheimer'S Amyloid-Beta 1-40 Peptide From Brain by LDL Receptor-Related Protein-1 at the Blood-Brain Barrier"; Journal of Clinical Investigation, vol. 106, No. 12, Dec. 2000, pp. 1489-1499, XP001077700.

Zlokovic et al; "Role of Low-Density Lipoprotein Receptor Related Protein-1 in Vascular Clearance of Amyloid Beta 1-40 Peptide From Brain"; Society for Neuroscience Abstracts, vol. 26, No. 1-2, 2000, pp. Abstract No. 275.18, XP001077059.

\* cited by examiner

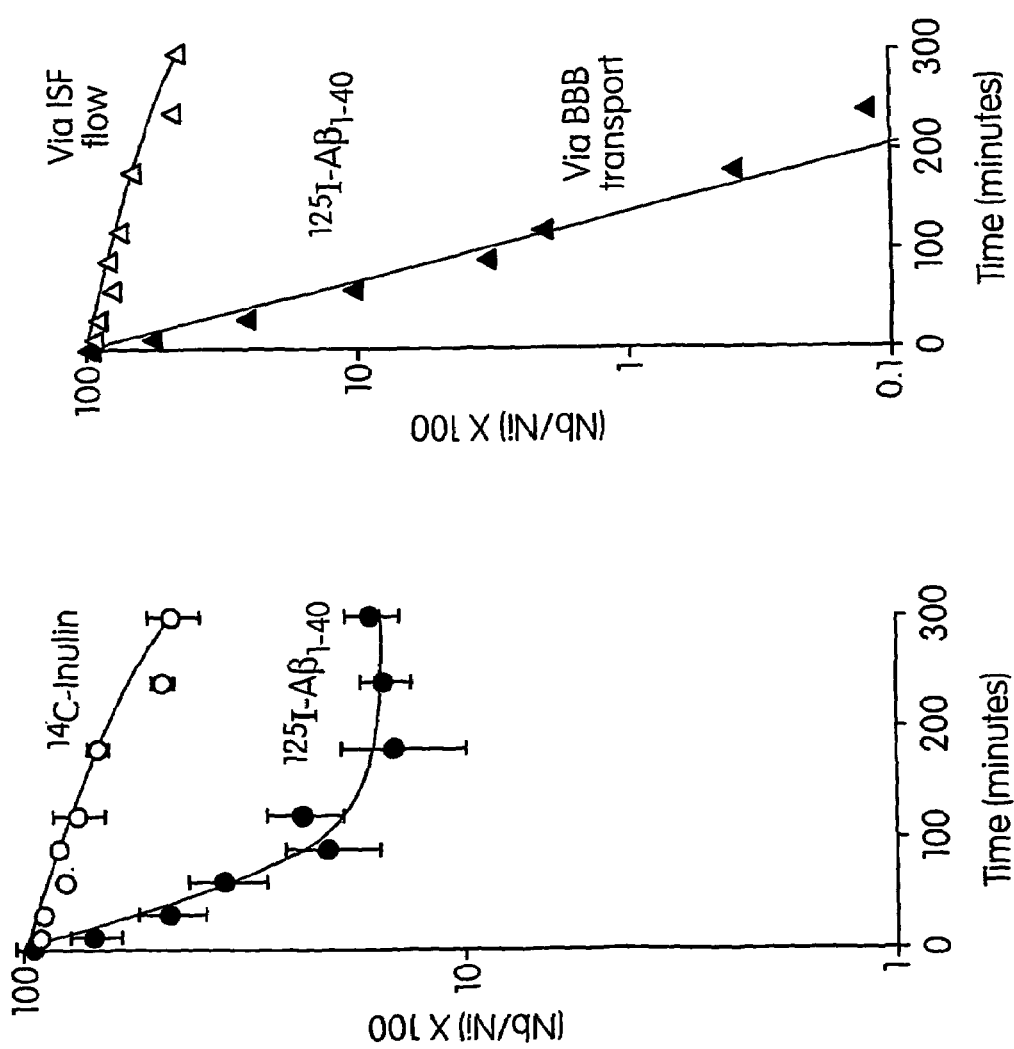

Control

AD

LOW-DENSITY LIPOPROTEIN RECEPTOR RELATED PROTEIN-1 (LRP-1) IN CLEARANCE OF ALZHEIMER'S AMYLOID-BETA PEPTIDE FROM THE CENTRAL NERVOUS SYSTEM

CROSS REFERENCE TO RELATED APPLICATION

This application is a national phase application of International Patent Appln. No. PCT/US01/16561 filed May 23, 2001, which designated the United States and was published in English, which claims the benefit of provisional U.S. Appln. No. 60/206,428, filed May 23, 2000, and U.S. Appln. No. 60/246,268, filed Nov. 6, 2000.

STATEMENT REGARDING FEDERALLY-SPONSORED RESEARCH

The U.S. government has certain rights in this invention as provided for by the terms of grants awarded by the National Institutes of Health.

FIELD OF THE INVENTION

The invention relates to the role of the vascular system in clearing Alzheimer's amyloid-β peptide (Aβ) from the central nervous system (CNS) as mediated by low-density lipoprotein receptor related protein-1 (LRP-1). Transport of Aβ occurs across the blood-brain barrier (BBB) to the systemic circulation, but the brain endothelium is compromised in Alzheimer's disease. The invention is used to diagnose symptomatic and asymptomatic individuals, to identify those at risk for disease or already affected thereby, to determine the stage of disease or its progression, to intervene earlier in or alter the disease's natural history, to provide a target for therapeutic or prophylactic treatments, to screen drugs or compare medical regimens, to determine the effectiveness of a drug or medical regimen, or any combination thereof.

BACKGROUND OF THE INVENTION

Deposition of amyloid-β peptide (Aβ) in brain occurs during normal aging and is accelerated in individuals with Alzheimer's disease (AD). Aβ is central to pathology of AD, and is the main constituent of brain parenchymal and vascular amyloid (1-6). Aβ extracted from senile plaques contains mainly $A\beta_{1-40}$ and $A\beta_{1-42}$ (7), while vascular amyloid is predominantly $A\beta_{1-39}$ and $A\beta_{1-40}$ (8). Several sequences of Aβ were found in both lesions (9-11). A major soluble form of Aβ, which is present in the blood, cerebrospinal fluid (CSF) (12-14) and brain (15-16) is $A\beta_{1-40}$. In the circulation, CSF and brain interstitial fluid (ISF), soluble Aβ may exist as a free peptide and/or associated with different transport binding proteins such as apolipoprotein J (apoJ) (17-18), apolipoprotein E (apoE) (19), transthyretin (20), lipoproteins (21), albumin (22), and alpha-2 macroglobulin ($\alpha_2$M) (23).

The neuronal theory argues that soluble brain-derived Aβ is a precursor of Aβ deposits. Neuronal cells secrete Aβ in culture (24), which supports this view. An increase in soluble Aβ in AD and Down's Syndrome brains precedes amyloid plaque formation (15, 25, 26), and correlates with the development of vascular pathology (27). Several cytosolic proteases that may degrade intracellular Aβ in vitro cannot degrade extracellular Aβ from brain ISF (28) or CSF (29) in vivo. An exception is enkephalinase that may degrade $A\beta_{1-42}$ from brain ISF (28). However, the physiological importance of this degradation in vivo remains still unclear since the peptide was studied at extremely high pharmacological concentrations (30).

It has been suggested that decreased clearance of Aβ from brain and CSF is the main cause of Aβ accumulation in sporadic AD (31). Since Aβ is continuously produced in the brain, a working hypothesis in this study was that efficient clearance mechanism(s) must exist at the blood-brain-barrier (BBB) to prevent its accumulation and subsequent aggregation in the brain. Cell surface receptors such as the receptor for advanced glycation end products (RAGE) (32-33), scavenger type A receptor (SR-A) (34), low-density lipoprotein receptor-related protein-1 (LRP-1) (35-38) and LRP-2 (39) bind Aβ at low nanomolar concentrations as free peptide (e.g., RAGE, SR-A), and/or in complex with $\alpha_2$M, apoE or apoJ (e.g., LRP-1, LRP-2). RAGE and SR-A regulate brain endothelial endocytosis and transcytosis of Aβ initiated at the luminal side of the BBB (33), while LRP-2 mediates BBB transport of plasma Aβ complexed to apoJ (39). The role of vascular receptors and BBB transport in the removal of brain-derived Aβ is unknown.

In the present study, a technique to measure brain tissue clearance in mice was developed based on a previous model in the rabbit (40). This technique was used to determine in vivo the efflux rates of $A\beta_{1-40}$ from the CNS as a function of time and concentration of peptide, and to characterize vascular transport and/or receptor-mediated efflux mechanism(s) involved in elimination of brain-derived Aβ across the BBB. The study focused on LRP-1 and its ligands, $\alpha_2$M and apoE because both promote Aβ clearance in smooth muscle cells (35), neurons (36, 38), and fibroblasts (37); and the apoE4 genetic locus is definitely, and the $\alpha_2$M genetic locus is possibly associated with increasing the risk for AD (41-42).

This study can be used to improve the understanding of the pathogenesis of Alzheimer's disease and mechanisms of disease. New and nonobvious modes of diagnosis and treatment are suggested by this discovery. Other advantages of the invention are discussed below or would be apparent to persons in the art from the disclosure herein.

SUMMARY OF THE INVENTION

In one embodiment of the invention, reagents are provided in kit form that can be used for performing the methods such as the following: diagnosis, identification of those at risk for disease or already affected, or determination of the stage of disease or its progression. In addition, the reagents may be used in methods related to the treatment of disease such as the following: evaluation whether or not it is desirable to intervene in the disease's natural history, alteration of the course of disease, early intervention to halt or slow progression, promotion of recovery or maintenance of function, provision of targets for beneficial therapy or prophylaxis, comparison of candidate drugs or medical regimens, or determination of the effectiveness of a drug or medical regimen. Instructions for performing these methods, reference values and positive/negative controls, and relational databases containing patient information (e.g., genotype, medical history, symptoms, transcription or translation yields from gene expression, physiological or pathological findings) are other products that can be considered aspects of the invention.

In other embodiments of the invention, these methods for diagnosis and treatment are provided. For screening of drugs and clinical trials, the respective drug and medical regimen selected are also considered embodiments of the invention. The amount and extent of treatment administered to a cell, tissue, or individual in need of therapy or prophylaxis is effective in treating the affected cell, tissue, or individual. One or more properties/functions of affected endothelium or cells thereof, or the number/severity of symptoms of affected individuals, may be improved, reduced, normalized, ameliorated, or otherwise successfully treated. The invention may be used alone or in combination with other known methods. Instructions for performing these methods, reference values and positive/negative controls, and relational databases containing patient information are considered further aspects of the invention. The individual may be any animal or human. Mammals, especially humans and rodent or primate models of disease, may be treated. Thus, both veterinary and medical methods are contemplated.

Further aspects of the invention will be apparent to a person skilled in the art from the following detailed description and claims, and generalizations thereto.

DESCRIPTION OF THE DRAWINGS

FIG. 1A shows time-disappearance curves of $^{14}C$-inulin (open circles) and $^{125}I$-A$\beta_{1-40}$ (60 nM; TCA-precipitable $^{125}I$-radioactivity, filled circles) from the CNS following simultaneous microinjections of tracers into the caudate nucleus in mice. Each point is mean±SD, from 3-7 animals. FIG. 1B shows two components of $^{125}I$-A$\beta_{1-40}$ efflux. Vascular transport across the BBB (filled triangles) and transport by ISF bulk flow (open triangles) were computed with eqs. 3 and 4, using data from FIG. 1A. FIG. 1C shows relative contributions to A$\beta_{1-40}$ efflux by transport across the BBB (open bar), diffusion by ISF bulk flow (closed bar), and retention (shaded bar) in the brain were studied at 60 nM concentrations and calculated from fractional coefficients given in Table 1.

DESCRIPTION OF THE INVENTION

Figure 2A:
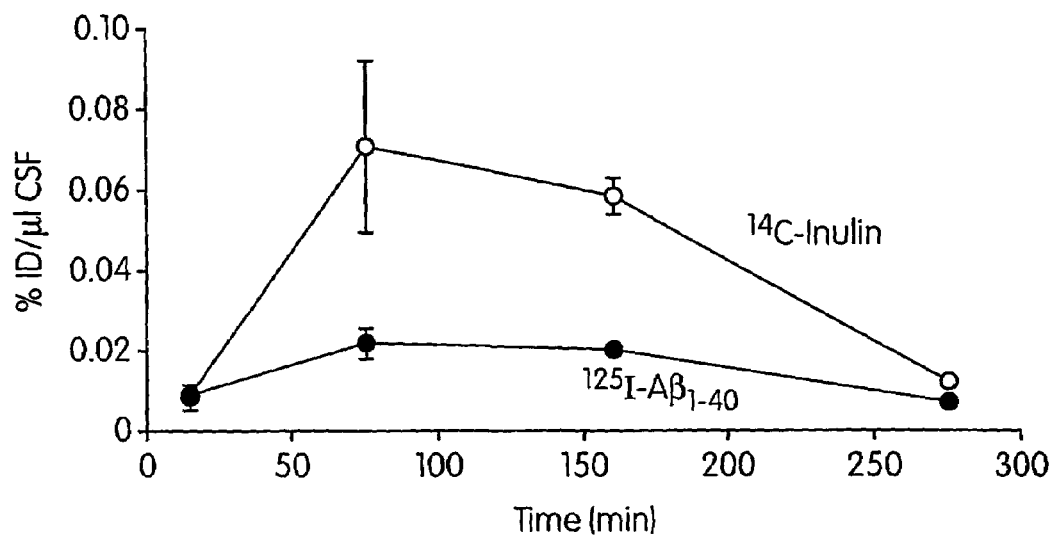
FIG. 2 shows time-appearance curves of $^{14}C$-inulin (open circles) and $^{125}I$-A$\beta_{1-40}$ (60 nM; TCA-precipitable $^{125}I$-radioactivity, filled circles) in the CSF (FIG. 2A) and plasma (FIG. 2B) following simultaneous microinjections of tracers into the caudate nucleus in mice. Values are expressed as % of injected dose (% ID); each point is mean±SD from 3-7 animals.

Elimination of amyloid-β peptide (AB) from the brain has been poorly understood. Following intracerebral microinjections in young mice, $^{125}I$-A$\beta_{1-40}$ was rapidly removed from the brain ($t_{1/2} \leq 25$ min) mainly by vascular transport across the blood-brain-barrier (BBB) ($\geq 74\%$). The efflux transport system for A$\beta_{1-40}$ at the BBB was half-saturated ($K_{0.5}$) at 15.3 nM and the maximal transport capacity was reached between 70 and 100 nM. A$\beta_{1-40}$ clearance was inhibited by the receptor associated protein (44%) and antibodies against low-density lipoprotein receptor-related protein-1, LRP-1 (58%) and alpha 2-macroglobulin, $\alpha_2 M$ (25%). Clearance was significantly reduced in young (30%) and old (46%) apolipoprotein E (apoE) knockout mice, and in old, wild type mice (55%). There was no evidence that Aβ was metabolized in brain interstitial fluid and degraded to smaller peptide fragments and amino acids prior to its transport across the BBB into the circulation. LRP-1, although abundant in brain microvessels in young mice, was down-regulated in older animals (45%). Down-regulation of vascular LRP-1 correlated with regional Aβ accumulation in brains of Alzheimer's disease patients. The BBB removes Aβ from the brain largely by an age-dependent, LRP-1-mediated transport mechanism that is influenced by $\alpha_2 M$ and/or apoE. This mechanism appears to be impaired in Alzheimer's disease at the level of transcript or protein abundance or receptor function (e.g., time required for receptor transcytosis or recycling, efficiency of ligand transport across the BBB).

Preparations of endothelial cells, isolated tissues, and in vitro cell cultures are provided from brain (e.g., microvasculature) or other organs (e.g., skin) of individuals at risk for Alzheimer's disease affected by the disease, or not. In particular, tissues like endothelium, smooth muscle, blood vessels and capillaries of the brain, temporal and leptomeningeal arteries, or any other tissues that express LRP-1 can be examined. Blood and bone marrow cells might also be used. They can be obtained as biopsy or autopsy material; cells of interest may be isolated therefrom and then cultured. Also provided are extracts of cells; at least partially purified DNA, RNA, and protein therefrom; and methods for their isolation. These reagents can be used to establish detection limits for assays, absolute amounts of gene expression that are indicative of disease or not, ratios of gene expression that are indicative of disease or not, and the significance of differences in such values. These values for positive and/or negative controls can be measured at the time of assay, before an assay, after an assay, or any combination thereof. Values may be recorded on storage medium and manipulated with computer software; storage in a database allows retrospective or prospective study. Gene expression (e.g., detected by antibody staining) and protein activity of LRP-1 (e.g., vascular clearance of AG from the brain to the systemic circulation) was decreased in individuals with Alzheimer's disease.

Polynucleotides representative of genes whose expression is decreased in Alzheimer's disease may be used to identify, isolate, or detect complementary polynucleotides by binding assays. Similarly, polypeptides representative of the gene products that are decreased in Alzheimer's disease may be used to identify, isolate, or detect interacting proteins by binding assays. Optionally, bound complexes including interacting proteins may be identified, isolated, or detected indirectly though a specific binding molecule (e.g., antibody) for the gene product that is decreased in Alzheimer's disease. For the receptor-ligand system studied here, LRP-1, apoE and $\alpha_2 M$ and are interacting proteins. Candidate compounds to treat Alzheimer's disease may interact with at least one gene, transcript, or protein which is a component of the receptor-ligand system to increase receptor activity (i.e., vascular clearance of Aβ), and be screened for their ability to provide therapy or prophylaxis. These products may be used in assays (e.g., diagnostic methods) or for treatment; conveniently, they are packaged as assay kits or in pharmaceutical form.

Assaying Polynucleotides or Polypeptides

Binding of polynucleotides or polypeptides may take place in solution or on a substrate. The assay format may or may not require separation of bound from not bound. Detectable signals may be direct or indirect, attached to any part of a bound complex, measured competitively, amplified, or any combination thereof. A blocking or washing step may be interposed to improve sensitivity and/or specificity. Attachment of a polynucleotide or polypeptide, interacting protein, or specific binding molecule to a substrate before, after, or during binding results in capture of an unattached species. See U.S. Pat. Nos. 5,143,854 and 5,412,087. Abundance may be measured at the level of protein and/or transcripts of a component of the receptor-ligand system.

Polynucleotide, polypeptide, or specific binding molecule may be attached to a substrate. The substrate may be solid or porous and it may be formed as a sheet, bead, or fiber. The substrate may be made of cotton, silk, or wool; cellulose, nitrocellulose, nylon, or positively-charged nylon; natural rubber, butyl rubber, silicone rubber, or styrenebutadiene rubber; agarose or polyacrylamide; silicon or silicone; crystalline, amorphous, or impure silica (e.g., quartz) or silicate (e.g., glass); polyacrylonitrile, polycarbonate, polyethylene, polymethyl methacrylate, polymethylpentene, polypropylene, polystyrene, polysulfone, polytetrafluoroethylene, polyvinylidenefluoride, polyvinyl acetate, polyvinyl chloride, or polyvinyl pyrrolidone; or combinations thereof. Optically-transparent materials are preferred so that binding can be monitored and signal transmitted by light.

Such reagents would allow capture of a molecule in solution by specific interaction between the cognate molecules and then could immobilize the molecule on the substrate. Monitoring gene expression is facilitated by using an array.

Polynucleotide, polypeptide, or specific binding molecule may be synthesized in situ by solid-phase chemistry or photolithography to directly attach the nucleotides or amino acids to the substrate. Attachment of the polynucleotide, polypeptide, or specific binding molecule to the substrate may be through a reactive group as, for example, a carboxy, amino, or hydroxy radical; attachment may also be accomplished after contact printing, spotting with a pin, pipetting with a pen, or spraying with a nozzle directly onto a substrate. Alternatively, the polynucleotide, polypeptide, or specific binding molecule may be reversibly attached to the substrate by interaction of a specific binding pair (e.g., antibody-digoxygenin/hapten/peptide, biotin-avidin/streptavidin, glutathione S transferase-glutathione, maltose binding protein-maltose, polyhistidine-nickel, protein A or G/immunoglobulin); cross-linking may be used if irreversible attachment is desired.

Changes in gene expression may be manifested in the cell by affecting transcriptional initiation, transcript stability, translation of transcript into protein product, protein stability, or a combination thereof. The abundance of transcript or polypeptide can be measured by techniques such as in vitro transcription, in vitro translation, Northern hybridization, nucleic acid hybridization, reverse transcription-polymerase chain reaction (RT-PCR), run-on transcription, Southern hybridization, cell surface protein labeling, metabolic protein labeling, antibody binding, immunoprecipitation (IP), enzyme linked immunosorbent assay (ELISA), radioimmunoassay (RIA), fluorescent or histochemical staining, microscopy and digital image analysis, and fluorescence activated cell analysis or sorting (FACS).

A reporter or selectable marker gene whose protein product is easily assayed may be used for convenient detection. Reporter genes include, for example, alkaline phosphatase, β-galactosidase (LacZ), chloramphenicol acetyltransferase (CAT), β-glucoronidase (GUS), bacterial/insect/marine invertebrate luciferases (LUC), green and red fluorescent proteins (GFP and RFP, respectively), horseradish peroxidase (HRP), β-lactamase, and derivatives thereof (e.g., blue EBFP, cyan ECFP, yellow-green EYFP, destabilized GFP variants, stabilized GFP variants, or fusion variants sold as LIVING COLORS fluorescent proteins by Clontech). Reporter genes would use cognate substrates that are preferably assayed by a chromogen, fluorescent, or luminescent signal. Alternatively, assay product may be tagged with a heterologous epitope (e.g., FLAG, MYC, SV40 T antigen, glutathione transferase, hexahistidine, maltose binding protein) for which cognate antibodies or affinity resins are available.

A polynucleotide may be ligated to a linker oligonucleotide or conjugated to one member of a specific binding pair (e.g., antibody-digoxygenin/hapten/peptide epitope, biotin-avidin/streptavidin, glutathione transferase or GST-glutathione, maltose binding protein-maltose, polyhistidine-nickel, protein A/G-immunoglobulin). The polynucleotid may be conjugated by ligation of a nucleotide sequence encoding the binding member. A polypeptide may be joined to one member of the specific binding pair by producing the fusion encoded such a ligated or conjugated polynucleotide or, alternatively, by direct chemical linkage to a reactive moiety on the binding member by chemical cross-linking. Such polynucleotides and polypeptides may be used as an affinity reagent to identify, to isolate, and to detect interactions that involve specific binding of a transcript or protein product of the expression vector. Before or after affinity binding of the transcript or protein product, the member attached to the polynucleotide or polypeptide may be bound to its cognate binding member. This can produce a complex in solution or immobilized to a support.

Construction of Expression Vector

An expression vector is a recombinant polynucleotide that is in chemical form either a deoxyribonucleic acid (DNA) and/or a ribonucleic acid (RNA). The physical form of the expression vector may also vary in strandedness (e.g., single-stranded or double-stranded) and topology (e.g., linear or circular). The expression vector is preferably a double-stranded deoxyribonucleic acid (dsDNA) or is converted into a dsDNA after introduction into a cell (e.g., insertion of a retrovirus into a host genome as a provirus). The expression vector may include one or more regions from a mammalian gene expressed in the microvasculature, especially endothelial cells (e.g., ICAM-2, tie), or a virus (e.g., adenovirus, adeno-associated virus, cytomegalovirus, herpes simplex virus, Moloney leukemia virus, mouse mammary tumor virus, Rous sarcoma virus, SV40 virus), as well as regions suitable for gene manipulation (e.g., selectable marker, linker with multiple recognition sites for restriction endonucleases, promoter for in vitro transcription, primer annealing sites for in vitro replication). The expression vector may be associated with proteins and other nucleic acids in a carrier (e.g., packaged in a viral particle).

The expression vector further comprises a regulatory region for gene expression (e.g., promoter, enhancer, silencer, splice donor and acceptor sites, polyadenylation signal, cellular localization sequence). Transcription can be regulated by tetracyline or dimerized macrolides. The expression vector may be further comprised of one or more splice donor and acceptor sites within an expressed region; a Kozak consensus sequence upstream of an expressed region for initiation of translation; downstream of an expressed region, multiple stop codons in the three forward reading frames to ensure termination of translation, one or more mRNA degradation signals, a termination of transcription signal, a polyadenylation signal, and a 3' cleavage signal. For expressed regions that do not contain an intron (e.g., a coding region from a cDNA), a pair of splice donor and acceptor sites may or may not be preferred. It would be useful, however, to include a mRNA degradation signal if it is desired to express one or more of the downstream regions only under the inducing condition. An origin of replication may be included that allows replication of the expression vector integrated in the host genome or as an autonomously replicating episome. Centromere and telomere sequences can also be included for the purposes of chromosomal segregation and protecting chromosomal ends from shortening, respectively. Random or targeted integration into the host genome is more likely to ensure maintenance of the expression vector but episomes could be maintained by selective pressure or, alternatively, may be preferred for those applications in which the expression vector is present only transiently.

An expressed region may be derived from a gene encoding LRP-1 or a ligand thereof in operative linkage with a regulatory region (e.g., constituitive, regulated, or endothelial-specific promoter and an optional enhancer). The expressed region may encode a translational fusion. Open reading frames of regions encoding a polypeptide and at least one heterologous domain may be ligated in register. If a reporter or selectable marker is used as the heterologous domain, then expression of the fusion protein may be readily assayed or localized. The heterologous domain may be an affinity or epitope tag.

Screening of Candidate Compounds

Another aspect of the invention are chemical or genetic compounds, derivatives thereof, and compositions including same that are effective in the treatment of Alzheimer's disease and individuals at risk thereof. The amount that is administered to an individual in need of therapy or prophylaxis, formulation, and timing and route of delivery is effective to reduce the number or severity of symptoms, to slow or limit progression of symptoms, to inhibit expression of one or more genes that are transcribed at a higher level in Alzheimers disease, to activate expression of one or more genes that are transcribed at a lower level in Alzheimer's disease, or any combination thereof. Determination of such amounts, formulations, and timing and route of drug delivery is within the skill of persons conducting in vitro assays, in vivo studies of animal models, and human clinical trials.

A screening method may comprise administering a candidate compound to an organism or incubating a candidate compound with a cell, and then determining whether or not gene expression is increased. The increase in activity may partially or fully compensate for a change that is associated with or may cause Alzheimer's disease. Gene expression may be increased at the level of rate of transcriptional initiation, rate of transcriptional elongation, stability of the transcript, translation of the transcript, rate of translational initiation, rate of translational elongation, stability of protein, rate of protein folding, proportion of protein in active conformation, functional efficiency of protein (e.g., activation or repression of transcription), or combinations thereof. See U.S. Pat. Nos. 5,071,773 and 5,262,300. High-throughput screening assays are possible.

The screening method may comprise incubating a candidate compound with a cell containing a reporter construct, the reporter construct comprising transcription regulatory region covalently linked in a cis configuration to a downstream gene encoding an assayable product; and measuring production of the assayable product. A candidate compound which increases production of the assayable product would be identified as an agent which activates gene expression. See U.S. Pat. Nos. 5,849,493 and 5,863,733.

The screening method may comprise measuring in vitro transcription from a reporter construct in the presence or absence of a candidate compound, the reporter construct comprising a transcription regulatory region; and determining whether transcription is altered by the presence of the candidate compound. In vitro transcription may be assayed using a cell-free extract, partially purified fractions of the cell-free extract, purified transcription factors or RNA polymerase, or combinations thereof. See U.S. Pat. Nos. 5,453,362; 5,534,410; 5,563,036; 5,637,686; 5,708,158; and 5,710,025.

Techniques for measuring transcriptional or translational activity in vivo are known in the art. For example, a nuclear run-on assay may be employed to measure transcription of a reporter gene. Translation of the reporter gene may be measured by determining the activity of the translation product. The activity of a reporter gene can be measured by determining one or more of the abundance of transcription of polynucleotide product (e.g., RT-PCR of GFP transcripts), translation of polypeptide product (e.g., immunoassay of GFP protein), and enzymatic activity of the reporter protein per se (e.g., fluorescence of GFP or energy transfer thereof).

Genetic Compounds for Treatment

Gene activation may be achieved by inducing an expression vector containing a downstream region related to a gene that is down regulated (e.g., the full-length coding region or functional portions of the gene; hypermorphic mutants, homologs, orthologs, or paralogs thereof or unrelated to the gene that acts to relieve suppression of gene activation (e.g., at least partially inhibiting expression of a negative regulator of the gene). Overexpression of transcription or translation, as well as overexpressing protein function, is a more direct approach to gene activation. Alternatively, the downstream expressed region may direct homologous recombination into a locus in the genome and thereby replace an endogenous transcriptional regulatory region of the gene with an expression cassette. In particular, gene expression of components of the receptor-ligand system transporting AB across the blood-brain barrier can be increased by introduction of an exogenous gene or activating an endogenous gene.

An expression vector may be introduced into a host mammalian cell or non-human mammal by a transfection or transgenesis technique using, for example, chemicals (e.g., calcium phosphate, DEAE-dextran, lipids, polymers), biolistics, electroporation, naked DNA technology, microinjection, or viral infection. The introduced expression vector may integrate into the host genome of the mammalian cell or non-human mammal. Many neutral and charged lipids, sterols, and other phospholipids to make lipid carrier vehicles are known. For example, neutral lipids are dioleoyl phosphatidylcholine (DOPC) and dioleoyl phosphatidyl ethanolamine (DOPE); an anionic lipid is dioleoyl phosphatidyl serine (DOPS); cationic lipids are dioleoyl trimethyl ammonium propane (DOTAP), dioctadecyldiamidoglycyl spermine (DOGS), dioleoyl trimethyl ammonium (DOTMA), and 1,3-di-oleoyloxy-2-(6-carboxy-spermyl)-propylamide tetra-acetate (DOSPER). Dipalmitoyl phosphatidylcholine (DPPC) can be incorporated to improve the efficacy and/or stability of delivery. FUGENE 6, LIPO-FECTAMINE, LIPOFECTIN, DMRIE-C, TRANSFECTAM, CELLFECTIN, PFX-1, PFX-2, PFX-3, PFX4, PFX-5, PFX4, PFX-7, PFX-8, TRANS-FAST, TFX-10, TFX-20, TFX-50, and LIPOTAXI lipids are proprietary formulations. The polymer may be polyethylene glycol (PEG) or polyethylenimine (PEI); alternatively, polymeric materials can be formed into nanospheres or microspheres. Naked DNA technology delivers the expression vector in plasmid form to a cell, where the plasmid may or may not become integrated into the host genome, without using chemical transfecting agents (e.g., lipids, polymers) to condense the expression vector prior to introduction into the cell.

Thus, a mammalian cell may be transfected with an expression vector; also provided are transgenic nonhuman mammals. In the previously discussed alternative, a homologous region from a gene can be used to direct integration to a particular genetic locus in the host genome and thereby regulate expression of the gene at that locus. Polypeptide may be produced in vitro by culturing transfected cells; in vivo by transgenesis; or ex vivo by introducing the expression vector into allogeneic, autologous, histocompatible, or xenogeneic cells and then transplanting the transfected cells into a host organism. Special harvesting and culturing protocols will be needed for transfection and subsequent transplantation of host stem cells into a host mammal. Immunosuppression of the host mammal post-transplant or encapsulation of the host cells may be necessary to prevent rejection.

The expression vector may be used to replace the function of a gene that is down regulated or totally defective or supplement function of a partially defective gene. Thus, the cognate gene of the host may be neomorphic, hypomorphic, hypermorphic, or normal. Replacement or supplementation of function can be accomplished by the methods discussed above, and transfected mammalian cells or transgenic non-human mammals may be selected for high expression (e.g., assessing amount of transcribed or translated product, or physiological function of either product) of the downstream region.

Formulation of Compositions

Compounds of the invention or derivatives thereof may be used as a medicament or used to formulate a pharmaceutical composition with one or more of the utilities disclosed herein. They may be administered in vitro to cells in culture, in vivo to cells in the body, or ex vivo to cells outside of the individual that may later be returned to the body of the same individual or another. Such cells may be diaggregated or provided as solid tissue.

Compounds or derivatives thereof may be used to produce a medicament or other pharmaceutical compositions. Use of compositions which further comprise a pharmaceutically acceptable carrier and compositions which further comprise components useful for delivering the composition to an individual are known in the art. Addition of such carriers and other components to the composition of the invention is well within the level of skill in this art.

A reduced fat diet or drug therapy to lower lipids (e.g., statins) may be used to alter LRP-1 receptor function in a beneficial manner. Alternatively, the drug may be used to increase gene expression of a component of the receptor-ligand system (e.g., enhancing transcription or translation). Reducing the systemic concentration of Aβ with antibody depletion or filtration of antibody-Aβ complexes may favor transport across the blood-brain barrier. Vasodilation, angiogenesis, neovascularization, and osmotic shock may be used to increase blood flow and thereby increase removal of Aβ from the brain to the systemic circulation. Another method for increasing removal may be to increase permeability of the blood vessel with known drugs (e.g., brady-kinin, histamine); tight junctions may be loosened or the width increased to increase permeability. Other methods for increasing transcytosis and recycling of LRP-1 may also be used (e.g., activators of cAMP signalling like theophylline). As illustrated by the latter, drugs may have one or more of the aforementioned beneficial affects. It should be noted that the modes of treatment described herein differ significantly from the mechanism described in U.S. Pat. No. 6,156,311 which identifies a role for low-density lipoprotein receptor related protein in endocytosis and degradation of Aβ.

Pharmaceutical compositions may be administered as a formulation adapted for passage through the blood-brain barrier or direct contact with the endothelium. Alternatively, pharmaceutical compositions may be added to the culture medium. In addition to the active compound, such compositions may contain pharmaceutically-acceptable carriers and other ingredients known to facilitate administration and/or enhance uptake (e.g., saline, dimethyl sulfoxide, lipid, polymer, affinity-based cell specific-targeting systems). The composition may be incorporated in a gel, sponge, or other permeable matrix (e.g., formed as pellets or a disk) and placed in proximity to the endothelium for sustained, local release. The composition may be administered in a single dose or in multiple doses which are administered at different times.

Pharmaceutical compositions may be administered by any known route. By way of example, the composition may be administered by a mucosal, pulmonary, topical, or other localized or systemic route (e.g., enteral and parenteral). The term "parenteral" includes subcutaneous, intradermal, intramuscular, intravenous, intraarterial, intrathecal, and other injection or infusion techniques, without limitation.

Suitable choices in amounts and timing of doses, formulation, and routes of administration can be made with the goals of achieving a favorable response in the individual with Alzheimer's disease or at risk thereof (i.e., efficacy), and avoiding undue toxicity or other harm thereto (i.e., safety). Therefore, "effective" refers to such choices that involve routine manipulation of conditions to achieve a desired effect.

A bolus administered over a short time once a day is a convenient dosing schedule. Alternatively, the effective daily dose may be divided into multiple doses for purposes of administration, for example, two to twelve doses per day. Dosage levels of active ingredients in a pharmaceutical composition can also be varied so as to achieve a transient or sustained concentration of the compound or derivative thereof in an individual, especially in and around vascular endothelium of the brain, and to result in the desired therapeutic response or protection. But it is also within the skill of the art to start doses at levels lower than required to achieve the desired therapeutic effect and to gradually increase the dosage until the desired effect is achieved.

The amount of compound administered is dependent upon factors known to a person skilled in the art such as bioactivity and bioavailability of the compound (e.g., half-life in the body, stability, and metabolism); chemical properties of the compound (e.g., molecular weight, hydrophobicity, and solubility); route and scheduling of administration; and the like. For systemic administration, passage of the compound or its metabolite through the blood-brain barrier is important. It will also be understood that the specific dose level to be achieved for any particular individual may depend on a variety of factors, including age, gender, health, medical history, weight, combination with one or more other drugs, and severity of disease.

The term "treatment" of Alzheimer's disease refers to, inter alia, reducing or alleviating one or more symptoms in an individual, preventing one or more symptoms from worsening or progressing, promoting recovery or improving prognosis, and/or preventing disease in an individual who is free therefrom as well as slowing or reducing progression of existing disease. For a given individual, improvement in a symptom, its worsening, regression, or progression may be determined by an objective or subjective measure. Efficacy of treatment may be measured as an improvement in morbidity or mortality (e.g., lengthening of survival curve for a selected population). Prophylactic methods (e.g., preventing or reducing the incidence of relapse) are also considered treatment. Treatment may also involve combination with other existing modes of treatment (e.g., ARICEPT or donepezil, EXELON or rivastigmine, anti-amyloid vaccine, mental exercise or stimulation). Thus, combination treatment with one or more other drugs and one or more other medical procedures may be practiced.

The amount which is administered to an individual is preferably an amount that does not induce toxic effects which outweigh the advantages which result from its administration. Further objectives are to reduce in number, diminish in severity, and/or otherwise relieve suffering from the symptoms of the disease as compared to recognized standards of care. The invention may also be effective against neurodegenerative disorders in general: for example, dementia, depression, confusion, Creutzfeldt-Jakob disease, Huntington's disease, Parkinson's disease, loss of motor coordination, multiple sclerosis, stroke, and syncope.

Production of compounds according to present regulations will be regulated for good laboratory practices (GLP) and good manufacturing practices (GMP) by governmental agencies (e.g., U.S. Food and Drug Administration). This requires accurate and complete recordkeeping, as well as monitoring of QA/QC. Oversight of patient protocols by agencies and institutional panels is also envisioned to ensure that informed consent is obtained; safety, bioactivity, appropriate dosage, and efficacy of products are studied in phases; results are statistically significant; and ethical guidelines are followed. Similar oversight of protocols using animal models, as well as the use of toxic chemicals, and compliance with regulations is required.

The following examples are merely illustrative of the invention, and are not intended to restrict or otherwise limit its practice.

EXAMPLES

Synthetic Peptide and Radio-Iodination

Peptide DAEFRHDSGYEVHHQKLVFFAEDVGSNK-GAIIGLMVGGVV (SEQ ID NO:1, $A\beta_{1-40}$) from amino acid residues 672-711 of Aβ-precursor protein-770 was synthesized at Yale University using N-t-butyloxycarbonyl chemistry and purified by HPLC. Aliquots of the final products were lyophilized and stored at −20° C. until use. Radio-iodination was carried out with Na[$^{125}$I] and Iodobeads (Pierce), and the resulting components resolved by HPLC (39). Aliquots of radiolabeled $A\beta_{1-40}$ were kept at −20° C. for a maximum of four weeks prior to use. The HPLC analysis confirmed that more than 99% of radioactivity was present in the form of non-oxidized monomeric peptide.

Brain Clearance Model in Mice

Male C57BL/6 wild type mice, 8-10 weeks old and 9-10 months old, and male apoE knockout mice (apoE KO) on a C57BL/6 background (Taconic Farm, Germantown, N.Y.), 8-10 weeks old and 9-10 months old, were studied. CNS clearance of radio-labeled $A\beta_{1-40}$ and the inert polar marker, inulin, was determined as described below (40,43).

A stainless steel guide cannula was implanted stereotaxically into the right caudate-putamen of anesthetized mice (60 mg/kg i.p. sodium pentobarbital). Coordinates for the tip of the cannula were 0.9 mm anterior and 1.9 mm lateral to bregma and 2.9 mm below the surface of the brain. The guide cannula and screw were fixed to the skull with methylmethacrylate (Plastics One, Roanoke, Va.) and a stylet introduced into the guide cannula. Animals were observed for one week prior to radiotracer studies.

For radioisotope injection, animals were re-anesthetized and an injector cannula (Plastic One, Roanoke, Va.) attached with 24G-TEFLON tubing (Small Parts, Miami Lake, Fla.) to a 10 μl gas-tight microsyringe (Hamilton, Reno, Nev.). The amount of injected tracers was determined accurately using a micrometer to measure linear displacement of the syringe plunger in the pre-calibrated micro-syringe. 0.5 μl of tracer fluid containing $^{125}$I-Aβ$_{1-40}$ at varying concentrations from 0.05 to 120 nM was injected over five minutes along with $^{14}$C-inulin. When the effects of different molecular reagents were tested, those were injected simultaneously with the radiolabeled peptides.

Time-response was studied with $^{125}$I-Aβ$_{1-40}$ from 10 min to 300 min and dose-dependent effects determined at 30 min. The effects of different molecular reagents that may potentially inhibit $^{125}$I-Aβ$_{1-40}$ clearance were studied at 30 min including: rabbit anti-human LRP-1 antibody designated as R777 that was affinity purified over Sepharose-LRP-1 heavy chain column as described (44) and that immunoprecipitates mouse LRP-1 as described (44) and blocks LRP-1-mediated uptake of APP and thrombospondin in murine fibroblasts (45-46); receptor associated protein (RAP) (provided by Dr. Bu, Washington University); rabbit anti-mouse ($α_2$M antibody designated as YNRMA2M that is specific for mouse $α_2$M as demonstrated by radial immunodiffusion and immunoel ctrophoresis (Accurate Scientific Corp, Westbury, N.Y.); rabbit anti-rat gp330 affinity purified IgG designated as Rb6286 that cross reacts with mouse LRP-2 as reported (47) (provided by Dr. Scott Argraves, University of S. Carolina); rabbit anti-human anti-RAGE antibody that cross-reacts with mouse RAGE (32) (provided by D. Stem, Columbia University) and fucoidan (Sigma, St. Louis, Mo.).

Tissue Sampling and Radioactivity Analysis

Brain, blood and CSF were sampled and prepared for radioactivity analysis. Degradation of $^{125}$I-Aβ$_{1-40}$ was initially studied by trichloroacetic acid (TCA) precipitation assay. Previous studies with $^{125}$I-Aβ$_{1-40}$ demonstrated an excellent correlation between TCA and HPLC methods (33, 48-51). Brain, plasma and CSF samples were mixed with TCA (final concentration 10%), centrifuged at 14,000 rpm at 4° C. for 8-10 minutes, and radioactivity in the precipitate, water and chloroform fractions determined in gamma counter (Wallac, Turku, Finland). The intactness of $^{125}$I-Aβ$_{1-40}$ injected into the brain was >97% by TCA analysis.

Degradation of $^{125}$I-Aβ$_{1-40}$ in brain was further studied by the HPLC and SDS-PAGE analyses. Following intracerebral injections of $^{125}$I-Aβ$_{1-40}$, brain tissue was homogenized in PBS containing protease inhibitors (0.5 mM phenylmethylsulfonyl fluoride, 1 μg/ml leupeptin and 1 mM p-aminobenzamidine) and centrifuged at 100,000 g for 1 hr at 4° C. The supernatant was then lyophilized. The resulting material was dissolved in 0.005% TFA in water, pH 2, before injection onto a C4 column (Vydac, The Separation Group, Hesperia, Calif.). The separation was achieved with a 30-min linear gradient of 25-83% acetonitrile in 0.1% TFA at a flow rate of 1 ml/min, as described (57). Under these conditions the Aβ$_{1-40}$ standard eluted at 14.5 min. Column eluants were monitored at 214 nm. The eluted fractions were collected and counted. The intactness of $^{125}$I-Aβ$_{1-40}$ injected into the brain by the HPLC analysis was >97% confirming the results of TCA analysis.

For SDS-PAGE analysis, TCA precipitated samples were resuspended in 1% SDS, vortexed and incubated at 5500 for 5 min, then neutralized, boiled for 3 min, homogenized and analyzed by electrophoresis in 10% Tris-tricine gels followed by fluorography. Lyophilized HPLC fractions were resuspended in sample buffer, neutralized, boiled and lectrophoresed as previously reported (39).

Calculations of Clearance Rates

The analysis of radioactivity-disappearance curves from the brain was as reported (40,43). The percentage of radioactivity remaining in the brain after microinjection was determined from eq. 1 as % Recovery in brain=$100 \times (N_b/N_i)$ where, $N_b$ is the radioactivity remaining in the brain at the end of the experiment and $N_i$ is the radioactivity injected into the brain.

In all calculations, the d.p.m. values for $^{14}$C-inulin and the c.p.m. values for TCA-precipitable $^{125}$I-radioactivity were used. Inulin was studied as a metabolically inert polar reference marker that is neither transported across the BBB nor retained by the brain (40); its clearance rate, i.e., $k_{inulin}$, provides a measure of the ISF bulk flow and is calculated as $N_{b(inulin)}/N_{i(inulin)} = \exp(-k_{inulin} * t)$ (2).

For Aβ, there are two possible physiological pathways of elimination—direct transport across the BBB into the bloodstream and elimination by ISF bulk flow into the CSF and cervical lymphatics. It is also possible that Aβ is retained within the brain either by binding to its cell surface receptors directly as a free peptide and/or by binding to different transport proteins. Thus, according to the model, the fraction of Aβ remaining in the brain can be expressed as $N_{b(A\beta)}/N_{i(A\beta)} = a_1 + a_2 * e^{-k1*t}$ (3), where $a_1 = k_2/(k_1+k_2)$ and $a_2 = k_1/(k_1+k_2)$, and $k_1$ and $k_2$ denote the fractional coefficients of total efflux from the brain and retention within the brain, respectively.

The fractional rate constant of Aβ efflux across the BBB from brain parenchyma can be calculated by knowing the fractional rate coefficient of total efflux of Aβ and inulin as $k_3 = k_1 - k_{(inulin)}$ (4), i.e., as the difference between the fractional rate constant for total efflux of Aβ and the fractional rate constant of inulin. The half-saturation concentration for the elimination of Aβ by transport across the BBB, 1(0.5, was calculated from the equation $[1-(N_b/N_i)]*100=Cl_{max}/(k_{0.5}+N_i)$ (5), where $Cl_{max}$ represents the maximal efflux capacity for the saturable component of Aβ clearance across the BBB corrected for peptide clearance by the ISF flow. $Cl_{max}$ is expressed as a percentage of the injected dose, $[1-(N_b/N_i)] \times 100$, cleared from brain by saturable BBB transport over 30 min.

The MLAB mathematical modeling system (Civilized Software, Silver Spring, Md.) was used to fit the compartmental model to the disappearance curves or percent recovery data with inverse square weighting.

Immunocytochemical Analysis in Mice

Expression of LRP-1 and $α_2$M in mouse brain was studied by immunohistochemical analysis. Fresh-frozen, acetone-fixed brain sections of 2-month-old and 9-month-old wild type mice, as well as apoE KO mice were stained using anti-human LRP R777 antibody that cross reacts with mouse LRP-1 (44-46) (1.5 mg/ml; 1:300 dilution), and anti-mouse $α_2$M antibody (as described above 1:250 dilution). R777 was affinity purified over Sepharose-LRP-1 heavy chain column, as described (44). The number of positive vessels was counted in ten random fields by two independent blinded observers and expressed as percentage per mm$^2$ of section. The extent and intensity of staining in cellular elements was quantitated using the Universal Imaging System and NIH imaging systems. Microvessels were carefully excluded from the quantitation by suitably varying the magnitudes of measurement. The relative intensity of cellular staining (excluding the microvasculature) in brain sections of young mice was arbitrarily normalized to 1 for purposes of comparison. Routine control sections included deletion of primary antibody, deletion of secondary anti-body and the use of an irrelevant primary antibody.

Neuropathological Analysis in Humans

Three AD patients and three neurologically normal, age-matched controls from the Alzheimers Disease Research Center (ADRC) of the University of Southern California were evaluated clinically and followed to autopsy. Included were 3 males and 3 females, ranging in age from 69 to 99 years.

Tissue blocks (1 cm$^3$) were obtained post-mortem (range 4-7 hrs; mean 5 hrs), fixed in 10% neutral buffered formalin, pH 7.3 (Sigma, St. Louis, Mo.) and embedded in paraffin or snap-frozen in liquid nitrogen-chilled isopentane. Tissues were sampled from the superior and middle frontal gyrus (Brodmann's area 10), and cerebellar hemisphere.

Sections were stained with either hematoxylin and eosin or thioflavin S, a modified Bielschowsky silver impregnation method (Gallyas stain). Thioflavin S stained sections were viewed through a Zeiss fluorescence microscope with a narrow band, blue/violet filter at 400 to 455 nm. Examination was performed by two independent observers. Diagnosis of AD was according to a modified CERAD (Consortium to Establish a Registry for Alzheimer's Disease) protocol (52).

For immunocytochemical analysis, air-dryed 10 μm cryostat sections of frontal cortex (Brodmann area 10) were used. Immunocytochemistry was performed using avidin-biotin peroxidase complexes (ABC method, Vector Laboratories, Burlingame, Calif.). Antibodies used include: $A\beta_{1-40}$ (Chemicon, Temecula, Calif.), rabbit anti-human, 1:1000 (1 mg/ml); $A\beta_{1-42}$, rabbit anti-human 1:1000 (1 mg/ml); the mouse monoclonal antibody to the heavy chain of human LRP-1 designated as 8G1 which is specific for human LRP-1 and recognizes an epitope on the 515 kDa subunit (53), 1:300 (1.5 mg/ml); and CD105 (clone SMG) (Serotec, Oxford, England), mouse anti-human 1:100 (0.1 mg/ml). For single staining with CD105 and LRP, after incubation with primary antibody, sections were washed three times in PBS, pH 7.4 and treated with biotinylated ant-mouse IgG for 30 minutes. After three washes in PBS, slides were incubated with avidin-biotin-HRP complex for 30 minutes and washed three times in PBS. Binding was detected with a Vector SG peroxidase detection kit (blue-gray). For double label, after incubation with $A\beta$ overnight at 4° C., sections were washed three times with PBS and treated with biotinylated anti-rabbit IgG, washed again, and binding was detected with Vector NovaRed. Following three washes in PBS, the second primary antibody (LRP or CD-105) was applied and staining performed as described for single label. Imaging was accomplished using a Zeiss Axiophot II microscope equipped with a Spot digital camera (Spot Diagnostics, Sterling Heights, Mich.).

Results

FIG. 1A illustrates brain radioactivity-disappearance curves of $^{14}$C-inulin and $^{125}$I-$A\beta_{1-40}$ (TCA-precipitable $^{125}$I-radioactivity) studied at a concentration of 60 nM. Clearance of inulin, a reference ECF maker that is neither transported across the BBB nor retained by the brain (40,43), approximated a single exponential decay, as expected from previous studies. The clearance curve reflecting total efflux from brain of $^{125}$I-$A\beta_{1-40}$ was bi-exponential and much lower than that for inulin, indicating significant biological transport of $A\beta_{1-40}$ out of the brain. The two components of $A\beta_{1-40}$ efflux, i.e., rapid elimination by vascular transport across the BBB into the blood and slow elimination through ISF flow, computed from FIG. 1A with eqs. 3 and 4 are illustrated in FIG. 1B. FIG. 1B indicates significantly higher clearance of $A\beta$ by BBB transport than by ISF bulk flow.

The half-time, $t_{1/2}$, for brain efflux of $A\beta_{1-40}$ and inulin calculated from FIG. 1A and eqs. 2 and 3 was 25.5±2.0 min and 239.0±12.5 min (Table 1), respectively, a 9.4-fold difference. The half-time of efflux of $A\beta_{1-40}$ across the BBB was 34.6±3.6 min, 6.9-fold faster than by ISF bulk flow. In addition to efflux, there was also a slow, time-dependent retention of $A\beta_{1-40}$ in brain parenchyma with a $t_{1/2}$ of 164.5 min. As shown in Table 1, the rate k (min$^{-1}$) of clearance of $A\beta_{1-40}$ from the brain was 7.9-fold higher than that for inulin. The relative contributions of $A\beta_{1-40}$ efflux at 60 nM by transport across the BBB and by ISF bulk flow based on 5 hr measurements were 73.8% and 10.7% respectively, while 15.6% of the dose remained sequestered within the CNS (FIG. 1C).

TABLE 1

Clearance rates, k, for $^{125}$I-$A\beta_{1-40}$ and $^{14}$C-Inulin

| Parameter | $^{125}$I-$A\beta_{1-40}$ | | $^{14}$C-Inulin | |
| --- | --- | --- | --- | --- |
| | k (min$^{-1}$) | $t_{1/2}$ (min) | k (min$^{-1}$) | $t_{1/2}$ (min) |
| Total Efflux | 0.0229 ± 0.0023* | 25.5 ± 2.0* | 0.0029 ± 0.0002 | 239 ± 12.5 |
| Transport by BBB | 0.0200 ± 0.0023 | 34.6 ± 3.6 | None | None |
| Transport by ISF | 0.0029 ± 0.0002 | 239 ± 12.5 | 0.0029 ± 0.0002 | 239 ± 12.5 |
| Retention in brain | 0.0042 ± 0.0005 | 164.5 ± 17.6 | None | None |

Data are mean ± SD from 38 individual experiments;
fractional coeffients, k, were calculated using equations 3 and 4;
*p < 0.05 bu Student' t-test.

Figure 2B:
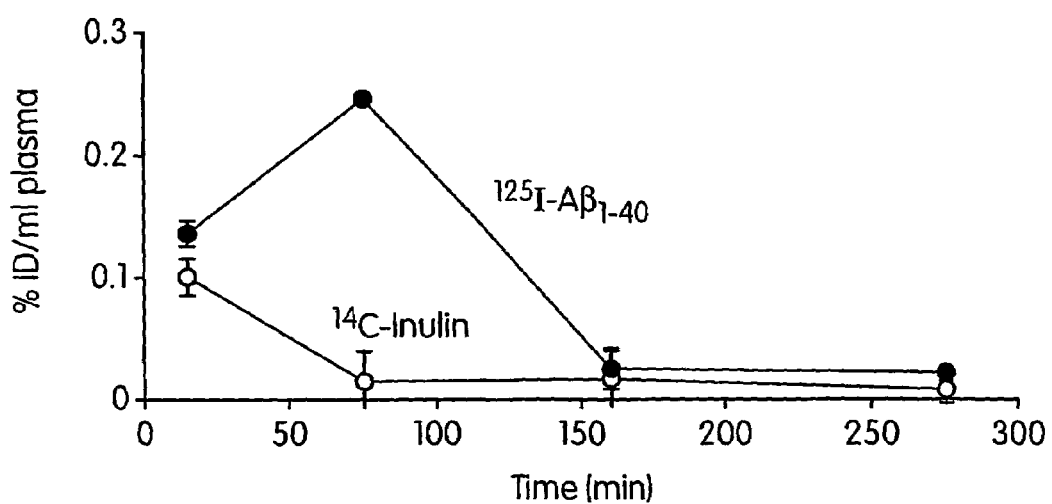

Following CNS injection, both tracers reached the CSF, and the CSF time-appearance curves are shown in FIG. 2A. The amount of $^{125}$I-$A\beta_{1-40}$ (TCA-precipitable $^{125}$I-radioactivity) determined in the CSF was lower than that for inulin at each time point, possibly reflecting an active clearance of $A\beta_{1-40}$ from the CSF, as suggested previously (28). It is noteworthy that at each studied time point the $^{125}$I-labeled material in the CSF was >96% TCA-precipitable indicating no degradation of the peptide. Both tracers also appeared in plasma (FIG. 2B), and higher levels of $^{125}$I-$A\beta_{1-40}$ TCA-precipitable radioactivity than of $^{14}$C-inulin radioactivity were consistent with active transport of $A\beta_{1-40}$ out of the CNS across the BBB. The absolute amounts of both tracers in the CSF and plasma were, however, low due to relatively rapid clearance from the CSF in comparison to slow ISF bulk flow (29), and significant systemic body clearance (48), respectively.

Figure 3A:
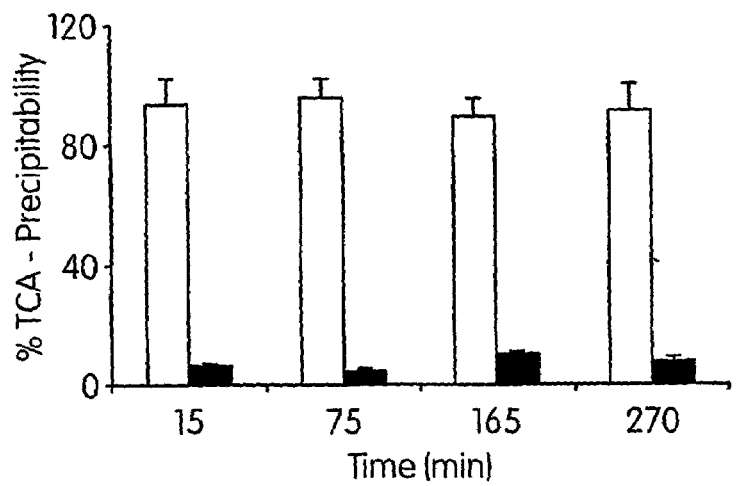
FIG. 3A shows brain TCA precipitable (open bars) and TCA non-precipitable $^{125}I$-radioactivity (solid bars) following intracerebral microinjections of $^{125}I$-A$\beta_{1-40}$ (60 nM) into the caudate nucleus in mice expressed as a percentage of total $^{125}I$-radioactivity in brain; mean±SD is from 3 to 5 animals.
Figure 3B:
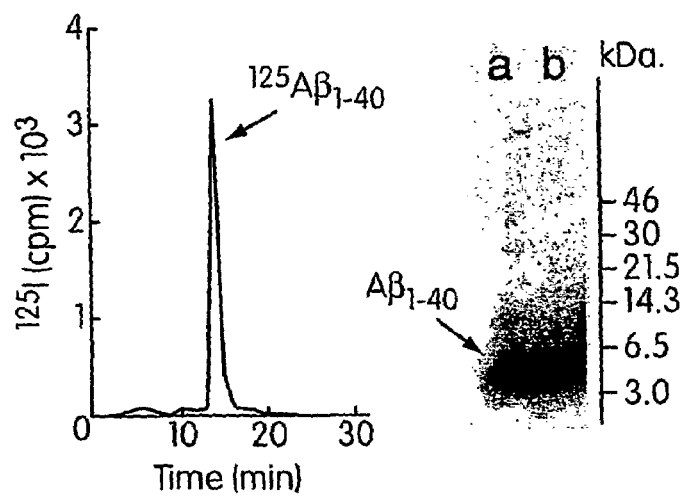
FIG. 3B shows a HPLC elution profile of brain tissue (right panel) 60 min following intracerebral microinjection of $^{125}I$-A$\beta_{1-40}$ (60 nM). Separation was performed for 30 mg of brain tissue on a reverse-phase HPLC column, using a 30-min linear gradient of 25-83% acetonitrile in 0.1% TFA, pH 2. $^{125}I$-A$\beta_{1-40}$ eluted at 52% corresponding to the elution time of AS, 40 standard. The left panel shows SDS/PAGE analysis of brain tissue supernatant at 30 min (lane a) and 60 min (lane b) following intracerebral microinjection of $^{125}I$-A$\beta_{1-40}$ (60 nM). The radioactivity in the brain was eluted as a single peak on HPLC with the same retention time as the A$\beta_{1-40}$ standard. Aliquots of lyophilized sample were subjected to 10% Tris Tricine SDS/PAGE, transferred to a nitrocellulose membrane, and exposed to x-ray film.
Figure 3C:
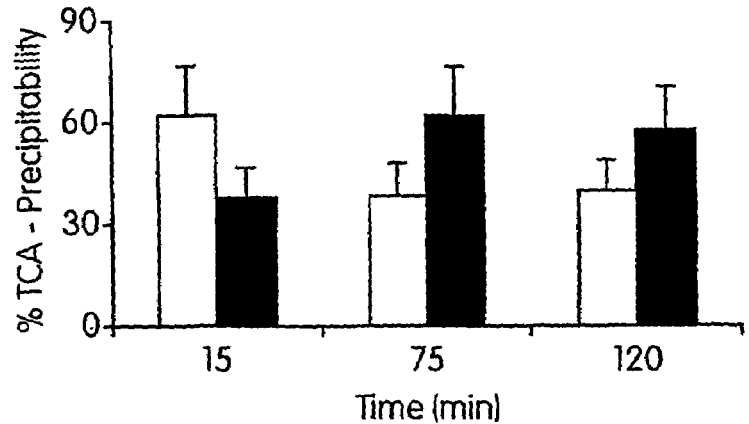
FIG. 3C shows plasma TCA precipitable (open bars) and TCA non-precipitable $^{125}I$-radioactivity (solid bars) following intracerebral micro-injections of $^{125}I$-A$\beta_{1-40}$ (60 nM) into the caudate nucleus in mice expressed as a percentage of total $^{125}I$-radioactivity in plasma; mean±SD is from 3 to 5 animals.

FIGS. 3A and 3B illustrate that $^{125}$I-$A\beta_{1-40}$ was not significantly degraded in brain ISF prior to its transport across the BBB as determined by TCA, HPLC and SDS-PAGE analysis of $^{125}$I-radioactivity in brain. The TCA analysis suggest that only 4.2 to 9.9% of $^{125}$I-radioactivity in brain was not TCA-precipitable at different time points within 270 min of intracerebral microinjection of $^{125}$I-$A\beta_{1-40}$ ((FIG. 3A). The HPLC analysis of brain radioactivity confirmed the TCA results by indicating that 93.7% of the peptide remains intact in brain ISF at 60 min (FIG. 3B, right). It is noteworthy that $^{125}$I-$A\beta_{1-40}$ was >97% intact at the time of injection as determined both by the HPLC and TCA analyses. The results were confirmed by SDS/PAGE analysis of lyophilized aliquots of HPLC peaks of brain homogenates at different time points after $^{125}$I-A$\beta_{1-40}$ injection that indicate single radioactive band at about 4 kDa (FIG. 3B, left). The identity of the radioactive components on gels as A$\beta_{1-40}$ peptide was confirmed by is Western blot analysis using anti-A$\beta$ antibody and enhanced chemiluminescence as a detection system. More than 96% of $^{125}$I-radioactivity in the CSF was TCA-precipitable at studied time points between 15 and 270 min. In contrast, degradation products of $^{125}$I-A$\beta_{1-40}$ were found in plasma (FIG. 3C); the amount of degraded $^{125}$I-A$\beta_{1-40}$ corresponding to TCA non-precipitable $^{125}$I-radioactivity increased from 37.6% to 58.3% from 15 to 120 min of intracerebral microinjection of intact $^{125}$I-A$\beta_{1-40}$ (FIG. 3C). It is noteworthy that the amount of radioactivity in plasma after 120 min was relatively small and approached the limits of sensitivity of the TCA assay.

Figure 4A:
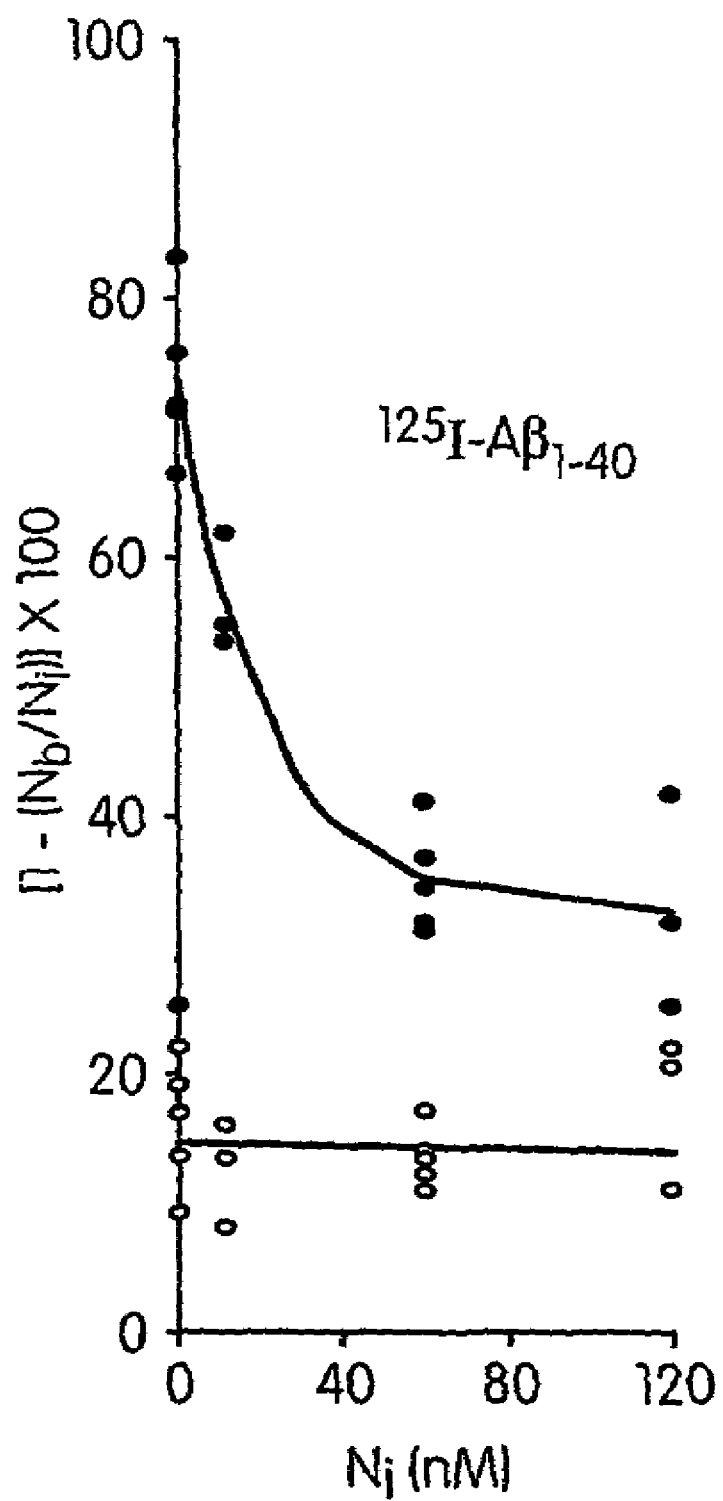
FIG. 4A shows concentration-dependent clearance of A$\beta_{1-40}$ from mouse brain. Clearance was determined 30 min after simultaneous microinjections of $^{125}I$-A$\beta_{1-40}$ at increasing concentrations (0.05 to 120 nM) along with $^{14}C$-inulin into the caudate nucleus. Clearance by BBB transport (filled circles) are shown separately from clearance by ISF bulk flow (open circles).

Clearance of A$\beta$ in young mice was concentration-dependent (FIG. 4A). The efflux transport system was half-saturated ($K_{0.5}$) at 15.3 nM of A$\beta_{1-40}$. The plateau or maximal clearance capacity was reached between 70 and 100 nM, and further increases in A$\beta$ concentration resulted in progressively greater retention of the peptide in the brain. In contrast, clearance of $^{14}$C-inulin did not change with increasing concentrations of A$\beta$ suggesting a physiologically intact BBB (FIG. 4A).

Figure 4B:
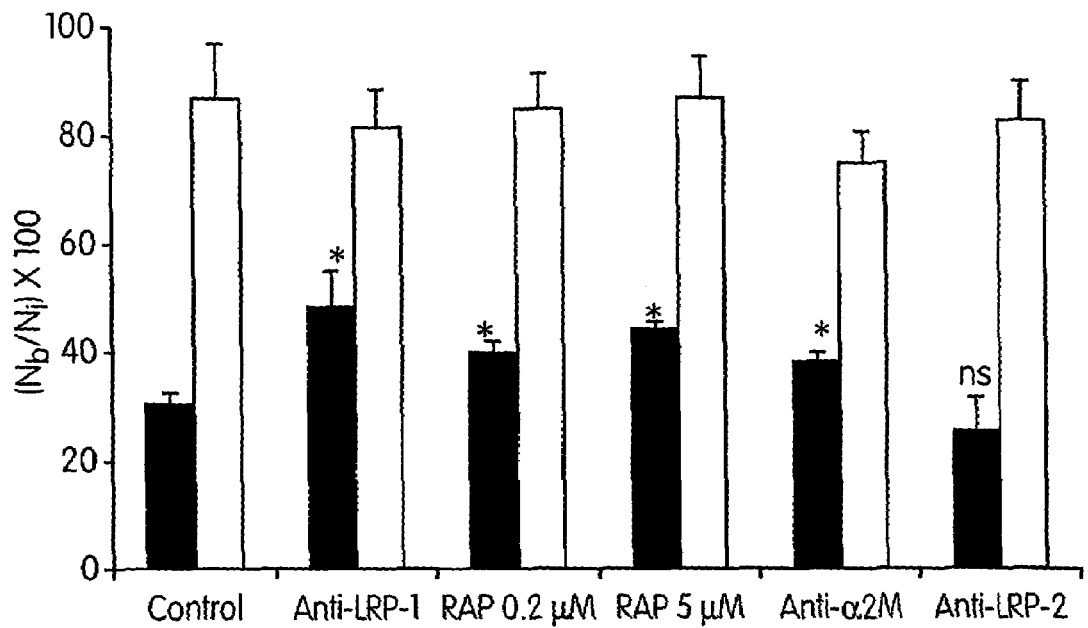
FIG. 4B shows the effects with (closed bars) or without (open bars) of anti-LRP-1 antibody R777 (60 µg/ml), RAP (0.2 and 5 µM), anti-α$_2$M antibody (20 µg/ml) and anti-LRP-2 antibody Rb6286 (60 µg/ml) on brain clearance of $^{125}I$-A$\beta_{1-40}$ at 12 nM determined 30 min after simultaneous $^{125}I$-A$\beta_{1-40}$/$^{14}C$-inulin microinjections.
Figure 4C:
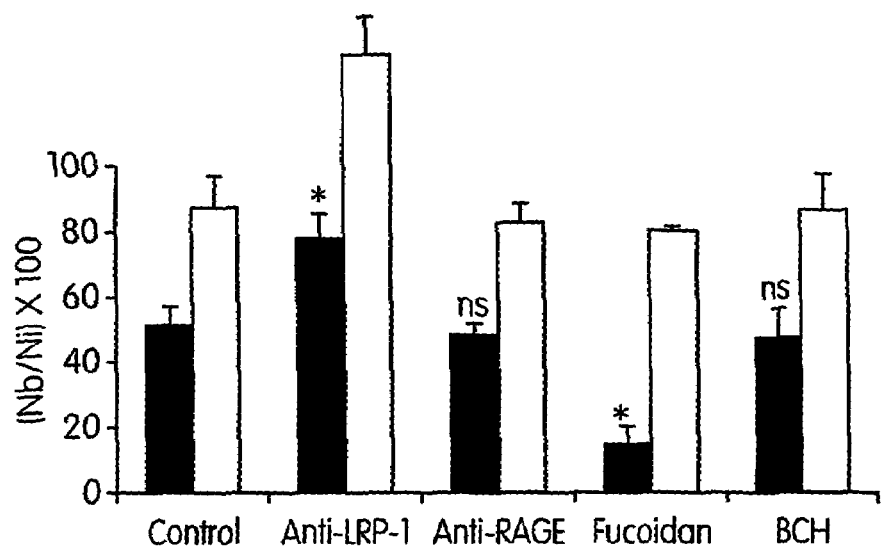
FIG. 4C shows effects of anti-LRP-1 antibody R777 (60 µg/ml), anti-RAGE antibody (60 µg/ml), fucoidan (100 µg/ml) and 2-aminobicyclo(2,2,1)heptane-2-carboxylic acid (BCH, 10 mM) on brain clearance of $^{125}I$-A$\beta_{1-40}$ at higher load of 60 nM determined 30 min after simultaneous $^{125}I$-A$\beta_{1-40}$/$^{14}C$-inulin microinjections. Mean±SD from 34 animals; *—p<0.05, ns—not significant.

The next set of experiments was designed to characterize the BBB transport system responsible for the transcytosis of A$\beta$. Brains were loaded with $^{125}$I-A$\beta_{1-40}$ either at 12 nM (FIG. 4B) or 60 nM (FIG. 4C) and clearance determined at 30 min in the absence (open bars) or the presence (solid bars) of several drugs that may act as potential inhibitors and/or competitors of export. FIG. 4B indicates that both LRP-1 antibody (60 μg/ml) and RAP (200 nM) produced significant, 58% and 30% respectively, reductions in A$\beta$ clearance from the brain in comparison to vehicle treated controls; a further decrease in A$\beta$ clearance to 44% was obtained by increasing the concentration of RAP to 5 μM. A significant 25% inhibition in A$\beta$ clearance was also obtained in the presence of anti-$\alpha_2$M antibody (20 μg/ml). In contrast, anti-LRP-2 antibody (FIG. 4B) and anti-RAGE antibody (FIG. 4C) did not affect A$\beta$ clearance. Fucoidan, a specific ligand for SR-A, produced a modest increase in the clearance, possibly by blocking the binding of A$\beta$ to parenchymal SR-A receptors, thereby allowing more peptide to be available for clearance. At higher A$\beta$ loads (FIG. 4C), anti-LRP-1 antibody produced a 53% decrease in clearance similar to that observed at a lower load (FIG. 4B), but A$\beta$ recovery approached that of $^{14}$C-inulin, suggesting drainage of the peptide almost exclusively through ISF bulk flow. Clearance of $^{14}$C-inulin was not affected by any of the studied molecular reagents. BCH, a substrate that specifically blocks L-system for amino acids, does not affect clearance of A$\beta$ across the BBB which excludes the possibility that $^{125}$I-A$\beta_{1-40}$ is degraded to $^{125}$I-tyrosine that is transported out of the CNS instead of $^{125}$I-A$\beta_{1-40}$.

Figure 5A:
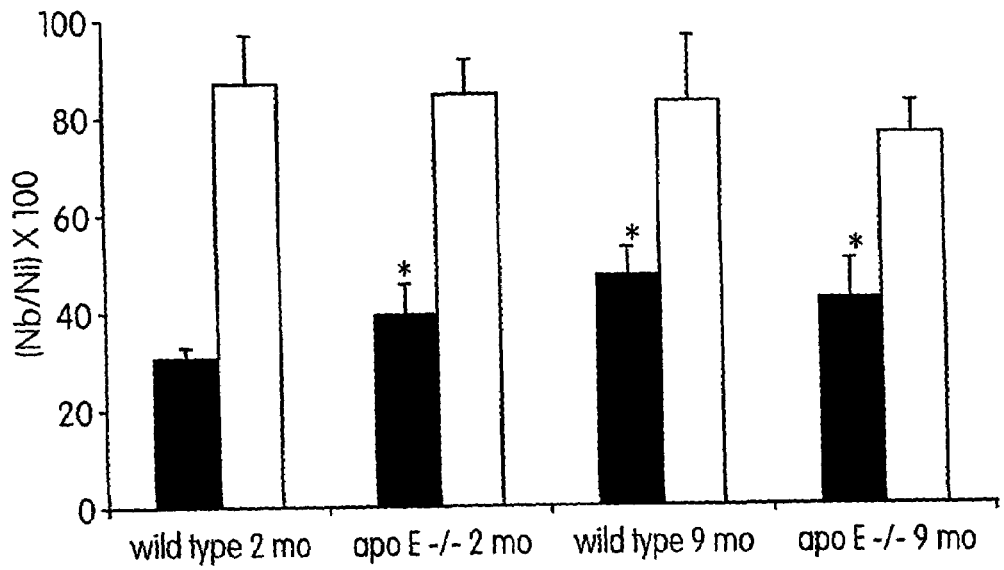
FIG. 5 shows the effect of apoE genotype and age on brain clearance of $^{125}I$-A$\beta_{1-40}$. Brain clearance of $^{125}I$-A$\beta_{1-40}$ in 2-month-old and 9-month-old wild-type mice and apoE KO mice studied at a lower load of $^{125}I$-A$\beta_{1-40}$ of 12 nM (FIG. 5A) and a higher load of 60 nM (FIG. 5B). In all studies, $^{125}I$-A$\beta_{1-40}$ (closed bars) and $^{14}C$-inulin (open bars) were injected simultaneously and clearance determined after 30 min. Mean±SD from 34 animals; *—p<0.05, ns—not significant in comparison to 2-month-old wild-type mice.
Figure 5B:
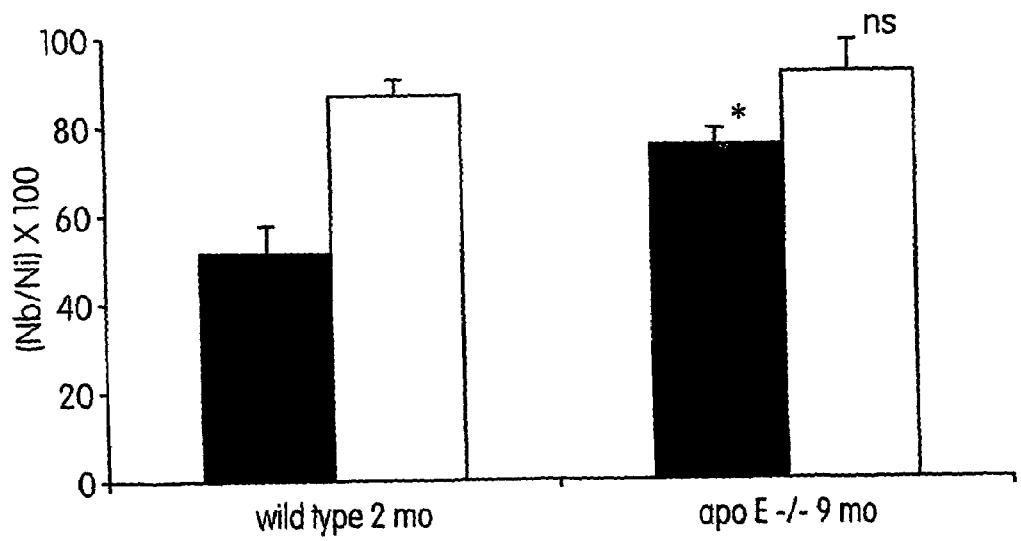

Next, the effect of apoE and aging was studied by determining A$\beta$ clearance in 2-month-old and 9-month-old apoE KO mice and wild type mice, using 12 nM (FIG. 5A) or 60 nM (FIG. 5B) of $^{125}$I-A$\beta_{1-40}$. FIG. 5A shows that the clearance of A$\beta$ was reduced by 30% in young apoE KO mice, and by about 55% and 40% in 9-month-old wild type and apoE KO mice, respectively. These results were confirmed at a higher load of A$\beta$, and observed decrease in clearance was 46% in 9-month-old apoE KO mice (FIG. 5B).

Figure 6A:
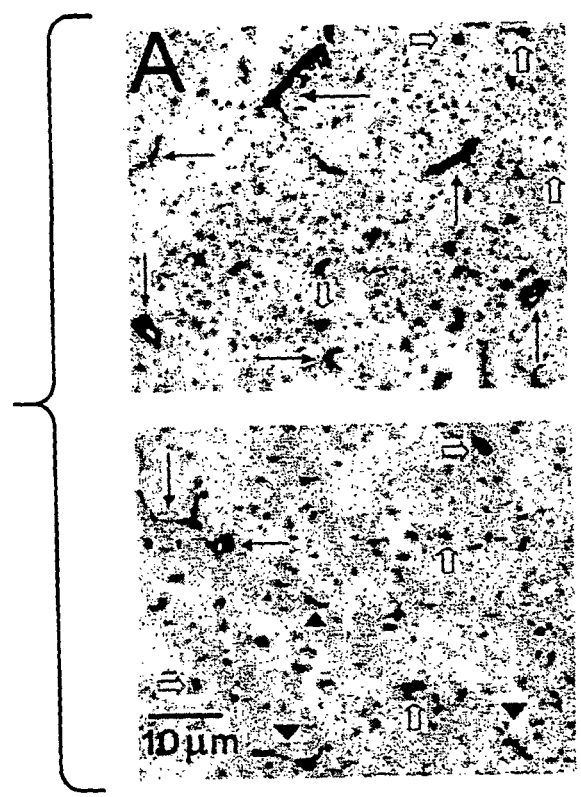
FIG. 6A shows LRP-1 immunoreactivity in brain microvessels of young (2-month-old; upper panel) and old (9-month-old; lower panel) wild-type mice. Many vessels in young mice stained positive for LRP-1 detected using anti-LRP-1 R777 antibody (5 µg/ml arrows), while there were relatively fewer positive vessels in old mice (arrows), and many weakly positive or negatively staining vessels (arrowheads). There was no significant difference in the staining of parenchymal cellular elements (open arrows) between the young and old mice.

Immunocytochemical studies confirmed abundant expression of LRP-1 in brain microvessels (including capillaries, small venules and arterioles) in 2-month-old mice (FIGS. 6A and 6B upper panels) in addition to significant parenchymal cellular (including neuronal) staining (FIG. 6A upper panel).

Figure 6B:
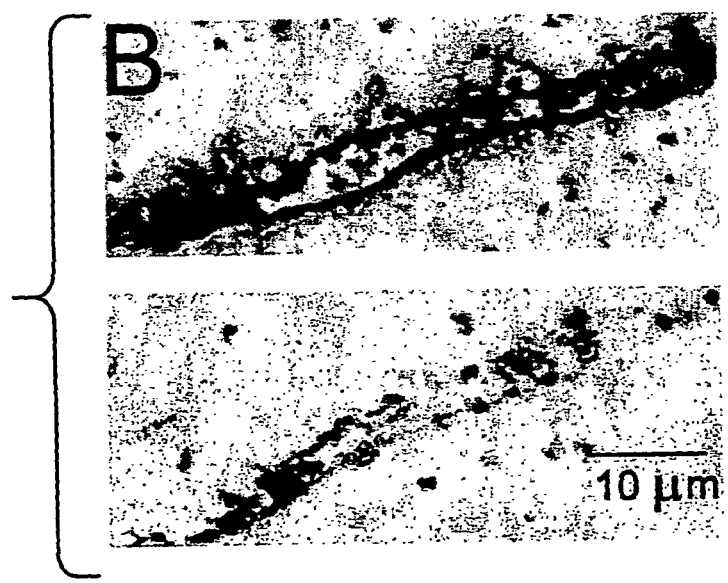
FIG. 6B shows vessels in young mice stained strongly positive (upper panel) compared to the faint staining seen in old mice (lower panel). In contrast.
Figure 6C:
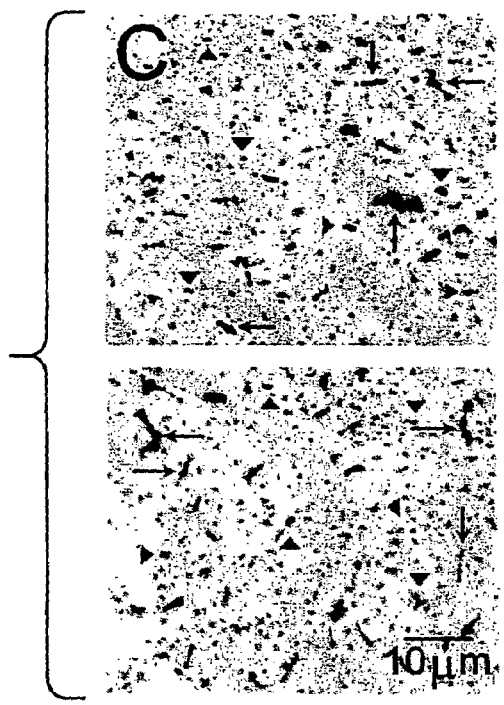
FIG. 6C shows there was no difference in staining for α$_2$M in brain cells (arrowheads) or microvessels (arrows) in young (upper panel) and old (lower panel) mice.
Figure 6D:
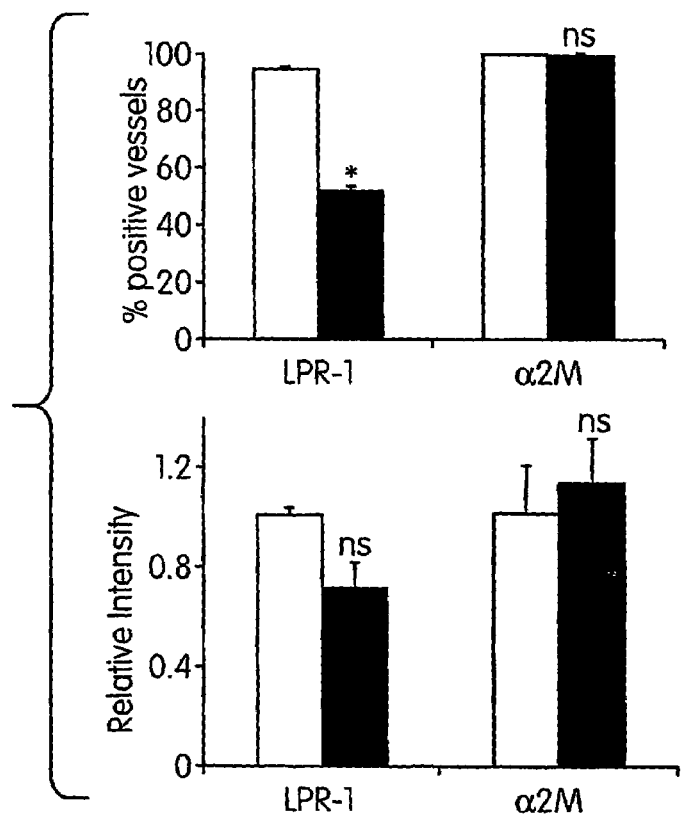
FIG. 6D compares LRP-1 and α$_2$M immunoreactivity in brain microvessels (upper panel) and parenchymal cellular elements (lower panel) in young wild-type mice (2 months, open bars) and old wild-type mice (9 months, closed bars). *—p<0.05, ns—not significant.

As shown in FIGS. 6A and 6B lower panels, there was a significant reduction in LRP-1 positive vessels in 9-month-old mice in comparison to 2-month-old mice; the number of LRP-1 positive vessels dropped from 94% in 2-month-old to 52% in 9-month-old mice (FIG. 6D upper panel). Quantitative analysis of LRP-1 positive parenchymal cells (excluding blood vessels) showed a trend towards reduced staining in older animals, though the difference was not statistically significant (FIG. 6D lower panel). Similarly, there was no significant difference in the number of $\alpha_2$M-positive microvessels or parenchymal cells in brain between young and old mice (FIG. 6C upper and lower panels, respectively, FIG. 6D lower panel). It is noteworthy that present staining for $\alpha_2$M was not able to distinguish between circulating $\alpha_2$M and $\alpha_2$M expressed on microvessels.

Figure 7A:
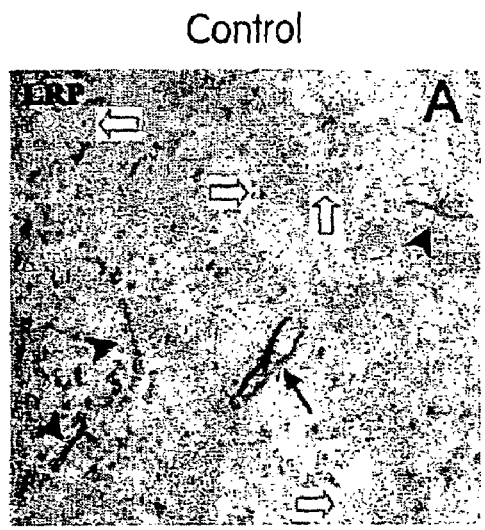
FIG. 7 shows LRP-1 expression in human frontal cortex. Brain sections (area 10) of controls (FIGS. 7A and 7C) reveal well-defined staining of capillaries (arrow-heads) and arterioles (arrows) by LRP-1 detected using anti-LRP-1 monoclonal 8G1 (5 µg/ml) (FIG. 7A) and CD105 (FIG. 7C). No Aβ staining was present in double- or serially-labeled sections. In contrast, double-labeled sections from AD patients (FIGS. 7B and 7D) show vessels and plaque cores positive with anti-A$\beta_{1-40}$ (brown stain) and reduced numbers and intensity of LRP-1 staining of vessels (FIG. 7B) and reduced numbers of CD105 labeled vessels (FIG. 7D).
Figure 7B:
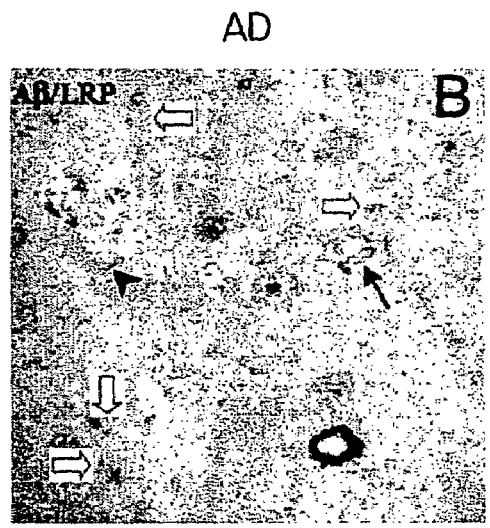
Figure 7C:
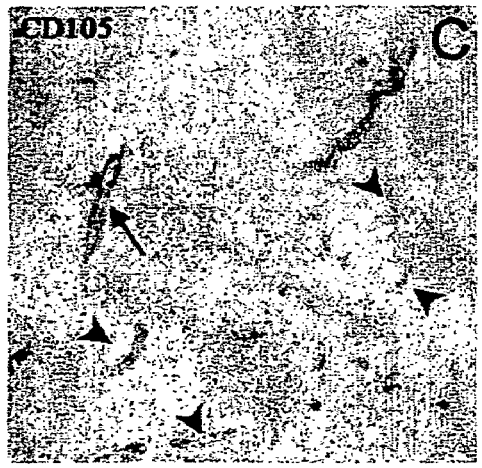
Figure 7D:
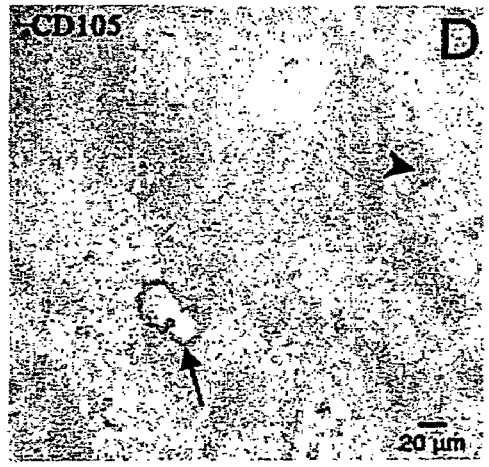

Frontal cortex of AD patients revealed moderate to marked neuritic plaques and A$\beta$ deposits in all AD patients and parenchymal and vascular amyloid in two of the three AD patients. Controls revealed no neuritic plaques or A$\beta$ in the parenchyma and only meningeal vascular A$\beta$ in one of the three patients. As seen in FIG. 7A, staining for LRP-1 in the frontal cortex of control patients revealed moderate vascular staining in capillaries and arterioles, as well as neuronal staining. There was reduced LRP-1 staining in AD tissues, including regions with A$\beta_{1-40}$ or A$\beta_{1-42}$ positive plaques and vessels (FIG. 7B). However, the immediate subcortical white matter showed more robust vascular staining for LRP-1, and absence of staining for A$\beta$, both in AD and controls. Anti-CD105, which identifies vascular endothelium, revealed ample staining of capillaries and arterioles of frontal cortex in controls and moderately reduced numbers of stained vessels in AD tissues. Cerebellum revealed equivalent vascular staining with anti-LRP-1 and CD105 in AD and control sections and no anti-A$\beta_{140}$ or A$\alpha_{1-42}$ positive staining was seen in either AD or control tissues.

Discussion

This study demonstrates the importance of vascular transport across the BBB in clearing A$\beta$ from the brain into circulation. Moreover, this transport mechanism is shown to be mediated mainly by LRP-1 in brain microvascular endothelium, and that transport of brain-derived A$\beta$ out of the CNS may be influenced by LRP-1 ligands, $\alpha_2$M and apoE. This vascular clearance mechanism for A$\beta$ is age-dependent, and lower clearance rates in older animals correlate with decreased vascular abundance of LRP-1.

The capability of BBB to remove A$\beta$ was significant in younger animals. The elimination time, $t_{1/2}$, for A$\beta_{1-40}$ at 60 nM was 25 min or 9.4-fold faster than for inulin, an ECF marker used to determine the ISF bulk flow rate (40). The major component of the CNS efflux of A$\beta$ was transport across the BBB into the vascular system. The clearance of A$\beta$ across the BBB was time- and concentration-dependent. At very low concentrations, i.e. <2 nM as found normally in mouse brain (54-55), A$\beta_{1-40}$ was eliminated from brain at a rate, on an average 3.5-fold faster than at a load of 60 nM that may compare to concentrations of A$\beta_{1-40}$ found in the brains of transgenic APP animals at 34 months (54-55). The efflux transport system was half-saturated at 15.3 nM of A$\beta_{1-40}$ and appears to be fully saturated at concentrations between 70 and 100 nM. Thus, this efflux transporter may be completely saturated by higher levels of A$\beta$ as found in the brains of older transgenic APP animals (54-55), which in turn may lead to vascular accumulation of A$\beta$ and development of prominent deposits of cerebrovascular amyloid, as recently described (56-57).

In this study, significant metabolism or degradation of A$\beta_{1-40}$ within 5 hrs was not observed, in contrast to a recent report suggesting that A$\beta_{1-42}$ is degraded by enkephalinase (neprilysin) in brain within minutes (28). There may be a possibility that A$\beta_{1-40}$ and A$\beta_{1-42}$ are differentially processed in the brain. The physiological relevance of the proposed degradation mechanism for A$\beta_{1-42}$ (28), however, remains unclear since the peptide was studied at extremely high concentrations of ~240 μM that are not found even in the brains with severe β-amyloidosis (30). As shown by pharmacological studies, these high concentrations of Aβ may impair local BBB integrity (58-59), which in turn may contaminate brain ISF with blood and/or plasma that possesses Aβ-degrading activity (48), as confirmed in this study.

Consistent with the hypothesis that cytosolic peptidases have little access to Aβ peptides secreted or injected into brain ISF (28) or CSF (29), it has been recently reported that insulin-degrading enzyme (IDE) cannot not degrade Aβ in brain in vivo following intracerebral injection of radiolabeled peptide (28). This is in contrast to in vitro degradation of $^{125}$I-A$\beta_{1-40}$ by IDE from brain and liver cytosol fractions (60). Since IDE is an intracellular protease, it is not surprising that IDE may not be able to process Aβ from brain ISF, in particular if peptide clearance is faster than its cellular uptake, as suggested here and in a previous study (28). It is noteworthy that brain endothelial cells in vitro (33) and astrocytes (61) do not catabolize Aβ, in contrast to activated microglial cells that secrete a specific metalloproteinase which degrades Aβ in vitro (61). Neuronal cells metabolize Aβ in vitro by an LRP-1-dependent mechanism that may require apoE or $\alpha_2$M (38). The rate of this degradation, however, is about 50 to 100-fold slower than by transport across the BBB in vivo.

Transport of Aβ out of the CSF was not associated with significant degradation of peptide in the CSF (29). Lower CSF levels of A$\beta_{1-40}$ in comparison to inulin may suggest an active transport of AS from the CSF to the blood, possibly across the choroid plexus or leptomeningeal vessels, as shown previously (29). Higher levels of radiolabeled Aβ in the plasma relative to inulin confirm vascular transport of the peptide out of the CNS. Although, present results indicate that brain-derived Aβ could contribute to the pool of circulating peptide, the degradation in plasma, systemic metabolism and body clearance tend to reduce the levels of circulating peptide, as shown previously (48). Under present experimental conditions the levels of radio-labeled Aβ in the circulation were two to three orders of magnitude lower than the brain levels, thus making re-entry of radiolabeled Aβ into the brain very unlikely since the blood-to-brain transport of Aβ normally operates down the concentration gradient (39, 62-65). In addition, the apoJ system that transports blood-borne Aβ into the brain is saturated under physiological conditions (64) that may facilitate the efflux of Aβ from brain. Previous studies have shown that circulating free Aβ is also metabolized during its transport across the BBB (48-49, 65-66), possibly by pericytes, which represent a major enzymatic barrier for the transport of several peptides and proteins across the BBB (67).

The affinity of neprilysin to its physiological substrates (e.g., enkephalins, tachykinins, atrial natriuretic peptide) and/or different synthetic peptides is in the low millimolar range (68). In contrast, the levels of Aβ in the brain are normally in low nanomolar range, and in transgenic models of brain amyloidosis they vary from 40 to 250 nmol/kg from 3 to 12 months (54). Thus, under physiological and/or pathological conditions, Aβ will likely bind to its high affinity cell surface receptors such as RAGE and/or SR-A and/or high affinity transport binding proteins, e.g., $\alpha_2$M, apoE and apoJ, that all react with low nanomolar level of peptide corresponding to their $K_D$ values.

In the present study, anti-LRP-1 antibodies inhibited A$\beta_{1-40}$ clearance by about 55%, both at lower (12 nM) and higher loads (60 nM) of the peptide, suggesting the involvement of LRP-1 in vascular elimination of Aβ from the brain. RAP, a chaperone protein that facilitates proper folding and subsequent trafficking of LRP-1 and LRP-2 (69), also inhibited Aβ clearance. RAP binds to multiple sites on LRP and antagonizes binding of all known LRP ligands to both LRP-1 and LRP-2 in vitro (69), as well as to LRP-2 in vivo at the blood side of the BBB (39). In the present study, RAP at higher concentrations produced comparable inhibition of Aβ clearance as an anti-LRP-1 antibody. It is interesting that anti-LRP-1 antibody almost completely inhibited vascular transport of Aβ at higher concentrations of peptide, which may indicate that LRP-1 could be of primary importance in eliminating the peptide from the brain. At a lower load of the peptide (i.e., 12 nM) though, neither of the molecular reagents was able to abolish clearance of Aβ, which suggests that in addition to LRP-1, there may be an alternative, highly sensitive BBB transport mechanism(s) that eliminates the peptide from the brain at very low concentrations. The molecular nature of this putative "second" transport system is not presently known, although present data suggest that RAGE and LRP-2 are unlikely to be involved in rapid elimination of Aβ from brain. The fact that fucoidan, an SR-A ligand moderately increased clearance of Aβ suggests that inhibition of SR-A receptors in brain may decrease CNS sequestration of the peptide, thus allowing more peptide to be available for enhanced clearance across the BBB.

The role of LRP-1 in promoting Aβ clearance in vitro in smooth muscle cells, neurons and fibroblasts by $\alpha_2$M and apoE has been suggested (35-38), although at significantly slower rates than across the BBB, as demonstrated in the present study. High affinity in vitro binding of Aβ to $\alpha_2$M and lipidated apoE3 and apoE4 and a lower affinity binding to delipidated apoE isoforms has been well documented (23, 70). Binding/uptake studies in mouse embryonic fibroblasts, wild type and deficient in LRP-1, confirmed that free Aβ is not a ligand for LRP-1 (37,45). The possible role of the two LRP-1 ligands in elimination of Aβ by vascular transport is suggested by inhibition of Aβ clearance with anti-$\alpha_2$M antibodies, and significantly reduced clearance in apoE KO animals by 30% and 46% at 2 months and 9 months of age, respectively, in comparison to wild type young controls. In relation to these findings, it is interesting to note that recent studies indicated that lack of endogenous mouse apoE in both the APP$^{V717F}$ and APPsw mouse models of AD results in less Aβ deposition and no fibrillar Aβ deposits in the brain (57, 71). This suggests that mouse apoE strongly facilitates Aβ fibrillogenesis. It is possible that mouse apoE also plays a role in clearance of soluble Aβ across the BBB as suggested by the current studies but that its ability to influence Aβ aggregation in APP transgenic mice is dominant. In contrast to the effects of mouse apoE, a recent study demonstrates that human apoE isoforms suppresses early Aβ deposition in APP$^{V717F}$ mice (72). Further studies in this model will be useful to determine whether this suppressive effect of human apoE isoforms on early Aβ deposition is secondary to effects on facilitating of Aβ transport across the BBB. Although the present study does not rule out the possibility that Aβ clearance by neurons, vascular smooth muscle cells and fibroblasts shown in vitro (35-38) may also occur in vivo, vascular transport across the BBB seems to be of primary importance for rapid elimination of Aβ from brain in vivo.

Since normal aging is associated with Aβ accumulation in brain (1), and there is a significant, time-dependent and progressive accumulation of Aβ with age in transgenic APP animals (54-55), it was hypothesized that the clearance mechanism of Aβ is impaired in older animals, and is also possibly impaired in elderly humans. The present findings of about 55-65% inhibition of Aβ clearance in 9-month-old wild type animals in comparison to young (2-month-old) animals confirmed this hypothesis. Immunocytochemical studies indicated a significant reduction in the number of LRP-1 positive cerebral blood vessels from 94% in 2-month-old to 52% in 9-month-old mice, which correlated well with the observed reductions in the clearance capacities between the two age groups. Interestingly, down-regulation of vascular LRP-1 correlated well with regional parenchymal and vascular accumulation of Aβ in brains of Alzheimer's patients compared to age-matched controls. In brain areas where LRP-1 vascular expression remains prominent, as in the white matter, no accumulation of Aβ was found in Alzheimer's brains.

These results are illustrative of the discovery that the vascular system plays an important role in regulating the levels of Aβ in the brain. The findings further suggest that if the levels of Aβ in brain extracellular space exceed the transport capacity of the clearance mechanism across the BBB, or if the vascular transport of the peptide were impaired, as for example, by down-regulation of LRP-1, this would result in accumulation of Aβ in the brain and possibly formation of amyloid plaques. Previous studies have demonstrated a major role of the BBB in determining the concentrations of Aβ in the CNS by regulating transport of circulating Aβ (33, 39, 49-51, 62-66). The present study extends this hypothesis by showing that vascular transport across the BBB out of the brain may represent a major physiological mechanism that prevents accumulation of Aβ and amyloid deposition in brain.

REFERENCES

1. Wisniewski et al. (1997) *Neurobiol. Dis.* 4:311-328.
2. Selkoe (1997) *Science* 275:630-631.
3. Selkoe (1998) *Trends Cell Biol.* 8:447-453.
4. Younkin (1998) *J. Physiol.* (Paris). 92:289-292.
5. Roses (1998) *Amer. J. Med. Gen.* 81:49-57.
6. Hardy et al. (1998) *Nature Neurosci.* 1:355-358.
7. Masters et al. (1985) *Proc. Natl. Acad. Sci. USA* 82:4245-4249.
8. Prelli et al. (1988) *J. Neurochem.* 51:648-651.
9. Roher et al. (1993) *Proc. Natl. Acad. Sci. USA* 90:10836-10840.
10. Shinkai et al. (1995) *Ann. Neurol.* 38:421-428.
11. Castano et al. (1996) *J. Biol. Chem.* 271:32185-32191.
12. Seubert et al. (1992) *Nature* 359:325-327.
13. Shoji et al. (1996) *Science* 258:126-129.
14. Vigo-Pelfrey et al. (1993) *J. Neurochem.* 61:965-968.
15. Tabaton et al. (1994) *Biochem. Biophys. Res. Commun.* 200:1598-1603.
16. Kuo et al. (1996) *J. Biol. Chem.* 271:4077-4081.
17. Ghiso et al. (1993) *Biochem. J.* 293:27-30.
18. Matsubara et al. (1995) *J. Biol. Chem.* 270:7563-7567.
19. Yang et al. (1997) *J. Neurochem.* 68:721-725.
20. Schwarzman et al. (1994) *Proc. Natl. Acad. Sci. USA* 91:8368-8372.
21. Matsubara et al. (1999) *Ann. Neurol.* 45:537-541.
22. Biere et al. (1996) *J. Biol. Chem.* 271:32916-32922.
23. Du et al. (1997) *J. Neurochem.* 69:299-305.
24. Busciglio et al. (1993) *Proc. Natl. Acad. Sci. USA* 90:2092-2096.
25. Naslund et al. (1994) *Proc. Natl. Acad. Sci. USA* 91:8378-8382.
26. Teller et al. (1996). *Nature Med.* 2:93-95.
27. Suzuki et al. (1994) *Am. J. Pathol.* 145:452-460.
28. Iwata et al. (2000) *Nature Med.* 6:143-150.
29. Ghersi-Egea et al. (1996) *J. Neurochem.* 67:880-883.
30. Zlokovic et al. (2000) *Nature Med.* 6:718-719.
31. Rosenberg et al. (2000) *Neurology.* 54:2045-2054.
32. Yan et al. (1996) *Nature* 382:685-691.
33. Mackic et al. (1998) *J. Clin. Invest* 102:734-743.
34. Paresce et al. (1996) *Neuron.* 17:553-565.
35. Urmoneit et al. (1997) *Lab. Invest.* 77:157-166.
36. Jordan et al. (1998) *J. Neurosci.* 18:195-204.
37. Narita et al. (1997) *J. Neurochem.* 69:1904-1911.
38. Qiu et al. (1999) *J. Neurochem.* 73:1393-1398.
39. Zlokovic et al. (1996) *Proc. Natl. Acad. Sci. USA* 93:4229-4236.
40. Yamada et al. (1991) *Am. J. Physiol.* 261:H1197-H1204.
41. Strittmater et al. (1996) *Annu. Rev. Neurosci.* 19:53-77.
42. Blacker et al. (1998) *Nature Gen.* 19: 357-360.
43. Zlokovic et al. (1987) *Exp. Neurol.* 98:436-452.
44. Kounas et al. (1992) *J. Biol. Chem.* 267:12420-12423.
45. Kounnas et al. (1995) *Cell* 82:331-340.
46. Mikhailenko et al. (1995) *J. Biol. Chem.* 270:9543-9549.
47. Kounnas et al. (1994) *In Vivo* 8:343-351.
48. Mackic et al. (1998) *J. Neurochem.* 70:210-215.
49. Maness et al. (1994) *Life Sci.* 55:1643-1650.
50. Poduslo et al. (1997) *Neurobiol. Dis.* 4:27-34.
51. Martel et al. (1997) *J. Neurochem.* 69:1995-2004.
52. Hyman et al. (1997) *J. Neuropathol. Exp. Neurol.* 56:1095-1097.
53. Strickland et al. (1990) *J. Biol. Chem.* 265:17401-17404.
54. Hsiao et al. (1996) *Science* 274:99-102.
55. Holcomb et al. (1998) *Nature Med.* 4:97-100.
56. Calhoun et al. (1999) *Proc. Natl. Acad. Sci. USA* 96:14088-14093.
57. Holtman et al. (2000) *Ann. Neurol.* 47:739-747.
58. Blanc et al. (1997) *J. Neurochem.* 68:1870-1881.
59. Thomas et al. (1996) *Nature* 380:168-171.
60. Kurochkin et al. (1994) *FEBS Lett.* 345:33-37.
61. Mentlein et al. (1998) *J. Neurochem.* 70:721-726.
62. Zlokovic et al. (1993) *Biochem. Biophys. Res. Commun.* 197:1034-1040.
63. Ghilardi et al. (1996) *Neuroreport.* 7:2607-2611.
64. Shayo et al. (1997) *Life Sci.* 60:L115-L118.
65. Martel et al. (1996) *Neurosci. Lett.* 206:157-160.
66. Saito et al. (1995) *Proc. Nat. Acad. Sci. USA* 92:10227-10231.
67. Krause et al. (1993) *Adv. Exp. Med. Biol.* 331:149-152.
68. Hersh et al. (1986) *J. Biol. Chem.* 261:6433-6437.
69. Bu et al. (1996) *J. Biol. Chem.* 271:22218-22224.
70. Tokuda et al. (2000) *Biochem. J.* 348:359-365.
71. Bales et al. (1999) *Proc. Natl. Acad. Sci. USA* 96:15233-15238.
72. Holtzman et al. (1999) *J. Clin. Invest* 103:R15-R21.

All references (e.g., articles, books, patents, and patent applications) cited above are indicative of the level of skill in the art and are incorporated by reference.

All modifications and substitutions that come within the meaning of the claims and the range of their legal equivalents are to be embraced within their scope. Moreover, "comprising" allows the inclusion of other elements in the claim, comprising essentially of allows the inclusion of other elements in the claim that do not materially affect operation of the invention, and no particular relationship between or among elements of a claim is meant unless such limitation is explicitly recited (e.g., arrangement of components in a product claim, order of steps in a method claim).

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

What is claimed is:

1. A method of at least diagnosing a human patient with Alzheimer's disease, said method comprising:
   (a) measuring at least abundance of low-density lipoprotein receptor related protein-1 (LRP-1), abundance of transcripts thereof, or LRP-1 receptor activity in a human patient,
   (b) comparing the abundance of LRP-1 protein, abundance of transcripts thereof, or activity of LRP-1 receptor in said human patient to at least an age-matched control not affected by Alzheimer's disease, and
   (c) at least diagnosing said human patient with Alzheimer's disease when the abundance of LRP-1 protein, abundance of transcripts thereof, or activity of LRP-1 receptor in said human patient is decreased relative to said age-matched control not affected by Alzheimer's disease;
   wherein LRP-1 mediated removal of amyloid-β peptide (Aβ) at the blood-brain barrier in the direction from brain to blood in said human patient is decreased as compared to an age-matched control not affected by Alzheimer's disease.

2. The method of claim 1, wherein the abundance of LRP-1 protein, abundance of transcripts thereof, or activity of LRP-1 receptor is measured at least in a brain vascular or systemic endothelial cell of said human patient.

3. The method of claim 1, wherein the abundance of LRP-1 protein, abundance of transcripts thereof, or activity of LRP-1 receptor is measured at least in a brain capillary, a temporal artery, a leptomeningeal artery, or at the blood-brain barrier of said human patient.

4. The method of claim 1, wherein the abundance of LRP-1 protein, abundance of transcripts thereof, or activity of LRP-1 receptor is measured at least in cultured endothelial cells of said human patient.

5. The method of claim 1, wherein the abundance of LRP-1 protein, abundance of transcripts thereof, or activity of LRP-1 receptor is measured at least in endothelium of said human patient.

6. The method of claim 1, wherein the abundance of LRP-1 protein, abundance of transcripts thereof, or activity of LRP-1 receptor is measured at least in blood or bone marrow of said human patient.

7. The method of claim 1, wherein the abundance of LRP-1 protein, abundance of transcripts thereof, or activity of LRP-1 receptor is measured in biopsy material.

8. The method of claim 1, wherein the abundance of LRP-1 protein, abundance of transcripts thereof, or activity of LRP-1 receptor is measured in autopsy material.

9. The method of claim 1, wherein the abundance of LRP-1 protein, abundance of transcripts thereof, or activity of LRP-1 receptor is measured in a cell extract.

10. A method of measuring low-density lipoprotein receptor related protein-1 (LRP-1) in a human patient with Alzheimer's disease, said method comprising measuring a decrease in LRP-1 mediated removal of amyloid-β peptide (Aβ) at the blood-brain barrier in the direction from brain to blood in said human patient relative to an age-matched control not affected by Alzheimer's disease.

11. The method of claim 10, wherein at least abundance of human LRP-1, abundance of transcripts thereof, or human LRP-1 receptor activity is decreased in said human patient.

* * * * *

SEQUENCE LISTING

```
<160> NUMBER OF SEQ ID NOS: 1

<210> SEQ ID NO 1
<211> LENGTH: 40
<212> TYPE: PRT
<213> ORGANISM: Human

<400> SEQUENCE: 1

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val
        35                  40
```